United States Patent
Yamada

(10) Patent No.: US 10,743,749 B2
(45) Date of Patent: Aug. 18, 2020

(54) SYSTEM AND METHOD FOR DETECTING OPTICAL PROBE CONNECTION

(71) Applicant: Canon U.S.A., Inc., Melville, NY (US)

(72) Inventor: Daisuke Yamada, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 148 days.

(21) Appl. No.: 16/131,662

(22) Filed: Sep. 14, 2018

(65) Prior Publication Data
US 2020/0085285 A1 Mar. 19, 2020

(51) Int. Cl.
| | |
|---|---|
| A61B 1/00 | (2006.01) |
| G02B 6/38 | (2006.01) |
| A61B 1/07 | (2006.01) |
| A61B 5/00 | (2006.01) |

(52) U.S. Cl.
CPC ...... *A61B 1/00165* (2013.01); *A61B 1/00057* (2013.01); *A61B 1/00126* (2013.01); *A61B 1/07* (2013.01); *A61B 5/0066* (2013.01); *G02B 6/3801* (2013.01)

(58) Field of Classification Search
None
See application file for complete search history.

(56) References Cited

U.S. PATENT DOCUMENTS

| | | |
|---|---|---|
| 4,560,286 A * | 12/1985 | Wickersheim ............ G01J 5/48 250/461.1 |
| 4,782,819 A | 11/1988 | Adair |
| 5,046,501 A | 9/1991 | Crilly |
| 5,106,387 A | 4/1992 | Kittrell et al. |
| 5,303,026 A | 4/1994 | Strobl et al. |
| 5,419,323 A | 5/1995 | Kittrell et al. |
| 5,439,000 A | 8/1995 | Gunderson et al. |

(Continued)

FOREIGN PATENT DOCUMENTS

JP 2016099253 A 5/2016

OTHER PUBLICATIONS

Motz J. et al "Optical fiber probe for biomedical Raman spectroscopy", Applied Optics, Jan. 20, 2004, pp. 542-554, vol. 43, No. 3.

(Continued)

*Primary Examiner* — Shawn Decenzo
(74) *Attorney, Agent, or Firm* — Canon U.S.A., Inc., IP Division

(57) ABSTRACT

A catheter system includes an electronic console; a catheter having a proximal end attachable to the console and a distal end configured to house therein an optical probe; an optical fiber configured to transmit from the console to the optical probe excitation radiation of a first wavelength, and configured to return to the console an optical response signal having a second wavelength longer than the first wavelength; a detector configured to detect intensity of the optical response signal; and a processor configured to determine, based on the detected intensity of the optical response signal, whether the catheter is properly connected to the console. The optical response signal is generated within the optical fiber itself in response to transmitting the excitation radiation therethrough. The optical response signal is an autofluorescence signal and/or Raman scattering signal generated from the optical fiber itself.

25 Claims, 11 Drawing Sheets

(56) References Cited

U.S. PATENT DOCUMENTS

| | | |
|---|---|---|
| 5,452,723 A | 9/1995 | Wu et al. |
| 5,562,100 A | 10/1996 | Kittrell et al. |
| 5,625,450 A | 4/1997 | Ikeno |
| 5,697,373 A | 12/1997 | Richards-Kortum et al. |
| 5,862,273 A * | 1/1999 | Pelletier ................. G01N 21/65 356/301 |
| 6,002,137 A | 12/1999 | Hayashi |
| 6,009,220 A | 12/1999 | Chan et al. |
| 6,026,319 A | 2/2000 | Hayashi |
| 6,069,691 A | 5/2000 | Rosow et al. |
| 6,070,096 A | 5/2000 | Hayashi |
| 6,095,982 A | 8/2000 | Richards-Kortum et al. |
| 6,317,624 B1 | 11/2001 | Kollias et al. |
| 6,373,567 B1 * | 4/2002 | Wise ................... G01J 3/1838 356/301 |
| 6,465,968 B1 | 10/2002 | Sendai |
| 6,516,217 B1 | 2/2003 | Tsujita |
| 6,574,502 B2 | 6/2003 | Hayashi |
| 6,697,657 B1 | 2/2004 | Shehada et al. |
| 6,763,261 B2 | 7/2004 | Casscells, III et al. |
| 6,800,057 B2 | 10/2004 | Tsujita et al. |
| 6,869,593 B2 | 3/2005 | Frangioni |
| 6,915,154 B1 | 7/2005 | Docherty et al. |
| 7,113,814 B2 | 9/2006 | Ward et al. |
| 7,132,645 B2 | 11/2006 | Korn |
| RE39,672 E | 6/2007 | Shehada et al. |
| 7,366,376 B2 | 4/2008 | Shishkov et al. |
| 7,428,048 B1 | 9/2008 | Farkas et al. |
| 7,449,153 B2 | 11/2008 | Sakai et al. |
| 7,483,554 B2 | 1/2009 | Kotsianti et al. |
| 7,587,236 B2 | 9/2009 | Demos et al. |
| 7,749,168 B2 | 7/2010 | Maschke et al. |
| 7,843,572 B2 | 11/2010 | Tearney et al. |
| 7,872,759 B2 | 1/2011 | Tearney et al. |
| 7,877,135 B2 | 1/2011 | Iketani et al. |
| 7,889,348 B2 | 2/2011 | Tearney et al. |
| 7,890,157 B2 | 2/2011 | Jo et al. |
| 7,952,706 B2 | 5/2011 | Ling et al. |
| 7,952,719 B2 | 5/2011 | Brennan, III |
| 8,035,819 B2 | 10/2011 | Zuluaga |
| 8,089,625 B2 | 1/2012 | Maruc et al. |
| 8,219,183 B2 | 7/2012 | Maschke et al. |
| 8,289,522 B2 | 10/2012 | Tearney et al. |
| 8,380,268 B2 | 2/2013 | Georgakoudi et al. |
| 8,473,036 B2 | 6/2013 | Gorman, III et al. |
| 8,571,640 B2 | 10/2013 | Holman |
| 8,582,096 B2 | 11/2013 | Chen et al. |
| 8,758,223 B1 | 6/2014 | Bodor et al. |
| 8,849,380 B2 | 9/2014 | Patwardhan |
| 8,928,889 B2 | 1/2015 | Tearney et al. |
| 8,953,911 B1 | 2/2015 | Xu et al. |
| 9,087,368 B2 | 7/2015 | Tearney et al. |
| 9,121,926 B2 | 9/2015 | Nair et al. |
| 9,179,845 B2 | 11/2015 | Farcy et al. |
| 9,286,673 B2 | 3/2016 | Begin et al. |
| 9,326,682 B2 | 5/2016 | Tearney et al. |
| 9,332,942 B2 | 5/2016 | Jaffer et al. |
| 9,557,154 B2 | 1/2017 | Tearney et al. |
| 2003/0077043 A1 | 4/2003 | Hamm et al. |
| 2004/0152992 A1 * | 8/2004 | Zeng ................... A61B 5/0071 600/476 |
| 2004/0156782 A1 | 8/2004 | Alam et al. |
| 2004/0241089 A1 | 12/2004 | Brister et al. |
| 2005/0273267 A1 | 12/2005 | Malone |
| 2007/0038124 A1 | 2/2007 | Fulghum, Jr. et al. |
| 2007/0078348 A1 | 4/2007 | Holman |
| 2007/0225579 A1 | 9/2007 | Lucassen et al. |
| 2008/0103384 A1 | 5/2008 | Pfister |
| 2008/0177145 A1 | 7/2008 | Furnish |
| 2008/0228086 A1 | 9/2008 | Ilegbusi et al. |
| 2008/0255426 A1 | 10/2008 | Iketani |
| 2008/0304074 A1 | 12/2008 | Brennan, III |
| 2009/0073439 A1 | 3/2009 | Tearney et al. |
| 2009/0153852 A1 | 6/2009 | Rensen |
| 2009/0203991 A1 | 8/2009 | Papaioannou et al. |
| 2009/0262993 A1 | 10/2009 | Kotsianti et al. |
| 2010/0092389 A1 | 4/2010 | Jaffer |
| 2010/0113906 A1 * | 5/2010 | Marple ................ A61B 5/0066 600/342 |
| 2010/0315632 A1 | 12/2010 | Brennan, III |
| 2011/0237895 A1 | 9/2011 | Yoshida et al. |
| 2011/0292400 A1 | 12/2011 | Fleming et al. |
| 2012/0080612 A1 * | 4/2012 | Grego ................. A61B 1/0008 250/458.1 |
| 2012/0101374 A1 | 4/2012 | Tearney et al. |
| 2012/0176613 A1 * | 7/2012 | Marple .................... G02B 6/32 356/301 |
| 2014/0276011 A1 | 9/2014 | Schmitt et al. |
| 2015/0080686 A1 | 3/2015 | Karlheinz et al. |
| 2015/0377787 A1 * | 12/2015 | Zeng ..................... G01N 21/64 356/301 |
| 2016/0228097 A1 | 8/2016 | Jaffer et al. |
| 2017/0135584 A1 | 5/2017 | Tearney et al. |
| 2017/0209049 A1 * | 7/2017 | Wang .................. A61B 5/0071 |
| 2018/0238806 A1 * | 8/2018 | Zhang ................. G01Q 30/025 |
| 2020/0008678 A1 * | 1/2020 | Barbagli .............. A61B 1/0051 |
| 2020/0008874 A1 * | 1/2020 | Barbagli ............... A61M 25/01 |

OTHER PUBLICATIONS

Walrafen, G. E., et al "Raman Spectral Characterization of Pure and Doped Fused Silica Optical Fibers", Applied Spectroscopy, 1975, pp. 337-344, vol. 29, No. 4.

Dochow, S., et al "Combined fiber probe for fluorescence lifetime and Raman spectroscopy", Anal Bioanal Chem, Nov. 2015, pp. 8291-8301, vol. 407, No. 27.

Ughi, G. J., et al "Dual modality intravascular optical coherence tomography (OCT) and near-infrared fluorescence (NIRF) imaging: a fully automated algorithm for the distance-calibration of NIRF signal intensity for quantitative molecular imaging", Int J Cardiovasc Imaging, Feb. 2015, pp. 259-238, vol. 31, No. 2.

Koskinas, K. C., et al., "Intracoronary imaging of coronary atherosclerosis: validation for diagnosis, prognosis and treatment", European Heart Journal, Dec. 2015, pp. 1-15.

Vinegoni, C., et al, "Indocyanine Green Enables Near-Infrared Fluorescence Imaging of Lipid-Rich, Inflamed Atherosclerotic Plaques", Sci Transl Med, May 25, 2011, vol. 3, No. 84.

Osborn, E. A., et al, "The Advancing Clinical Impact of Molecular Imaging in CVD", JACC: Cardiovascular Imaging, Dec. 2013, pp. 1327-1341, vol. 6, No. 12.

Lee, S., et al, "Fully Integrated High-Speed Intravascular Optical Coherence Tomography/Near-Infrared Fluorescence Structural/Molecular Imaging in Vivo Using a Clinically Available Near-Infrared Fluorescence-Emitting Indocyanine Green to Detect Inflamed Lipid-Rich Atheromata in Coronary-Sized Vessels", Circ Cardiovasc Interv, 2014, pp. 560-569.

Hara, T., et al, "Molecular imaging of fibrin deposition in deep vein thrombosis using a new fibrin-targeted near-infrared fluorescence (NIRF) imaging strategy", JACC Cardiovasc Imaging, Jun. 2012, pp. 607-615, vol. 5, No. 6.

Jo, J. A., et al, "Simultaneous morphological and biotechnical endogenous optical imaging of atherosclerosis", European Heart Journal—Cardiovascular Imaging, 2015, pp. 910-918, vol. 16.

Fard, A. M., et al, "Optical coherence tomography- near infrared spectroscopy system and catheter for intravascular imaging", Optics Express, Dec. 16, 2013, pp. 30849-30858 vol. 21, No. 25.

Phipps, J., et al, "Fluorescence lifetime imaging for the characterization of the biochemical composition of atherosclerotic plaques", Joural of Biomedical Optics, Sep. 2011, vol. 16, No. 9.

Scepanovic, O. B., et al, "Multimodal spectroscopy detects features of vulnerable atherosclerotic plaque", Journal of Biomedical Optics, Jan. 2011, vol. 16, No. 1.

Ughi, G. J., et al, "Clinical Characterization of Coronary Atherosclerosis With Dual-Modality OCT and Near-Infrared Autofluorescence Imaging", JACC Cardiovascular Imaging, 2016.

(56) References Cited

OTHER PUBLICATIONS

Yoo, H., et al, "Intra-arterial catheter for simultaneous microstuctural and molecular imaging in vivo", Nature Medicine, Dec. 2011, pp. 1680-1685, vol. 17, No. 12.

* cited by examiner

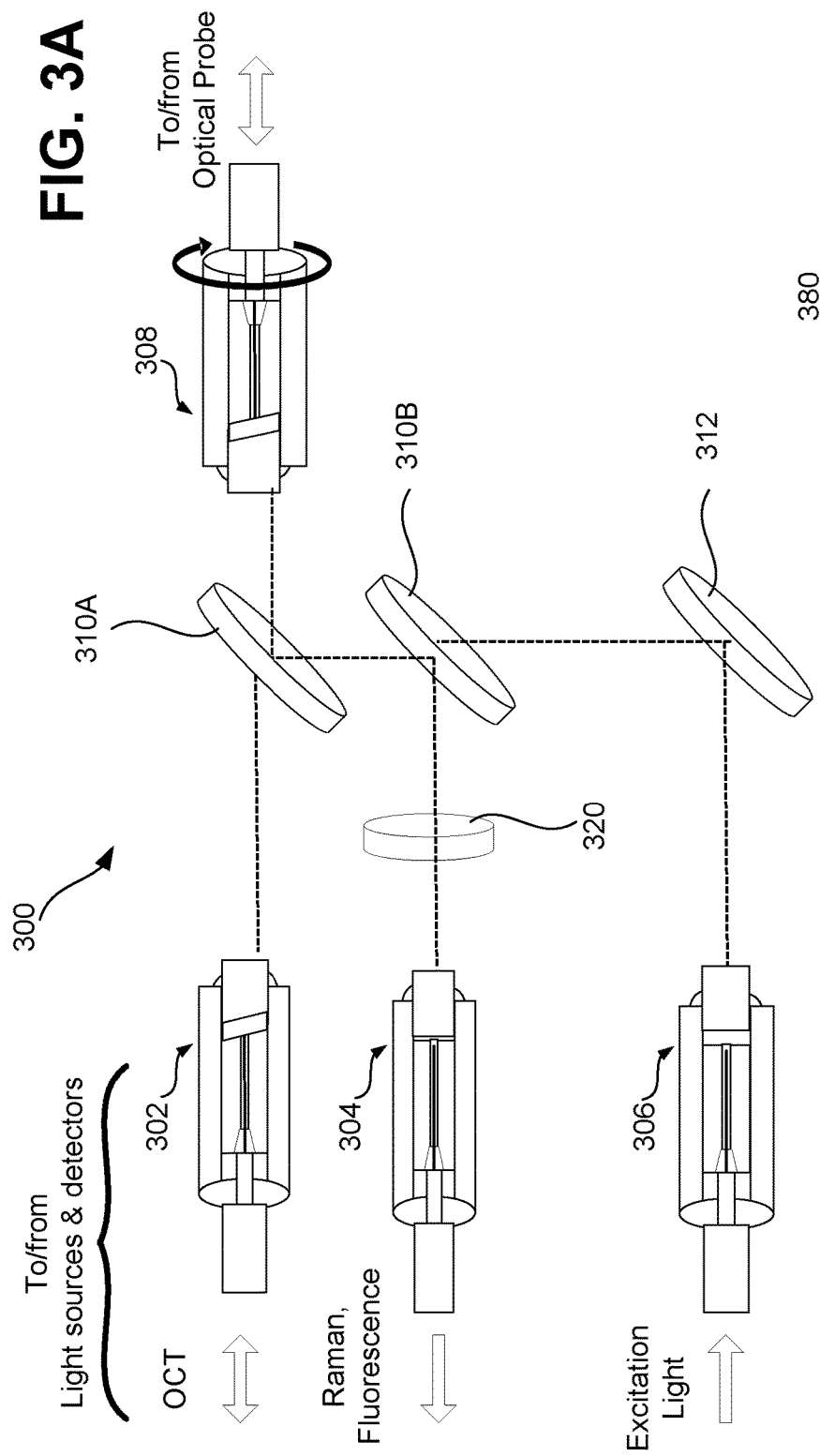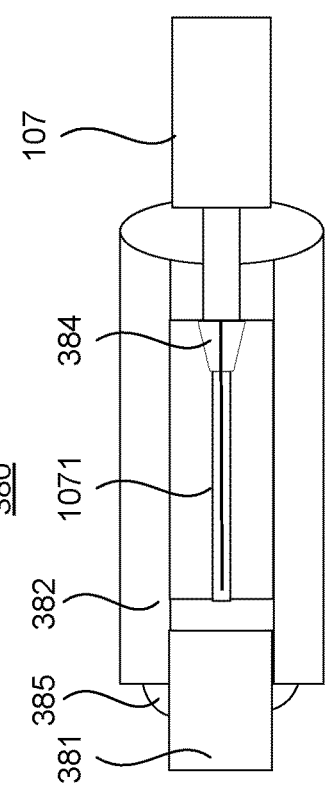

FIG. 5D
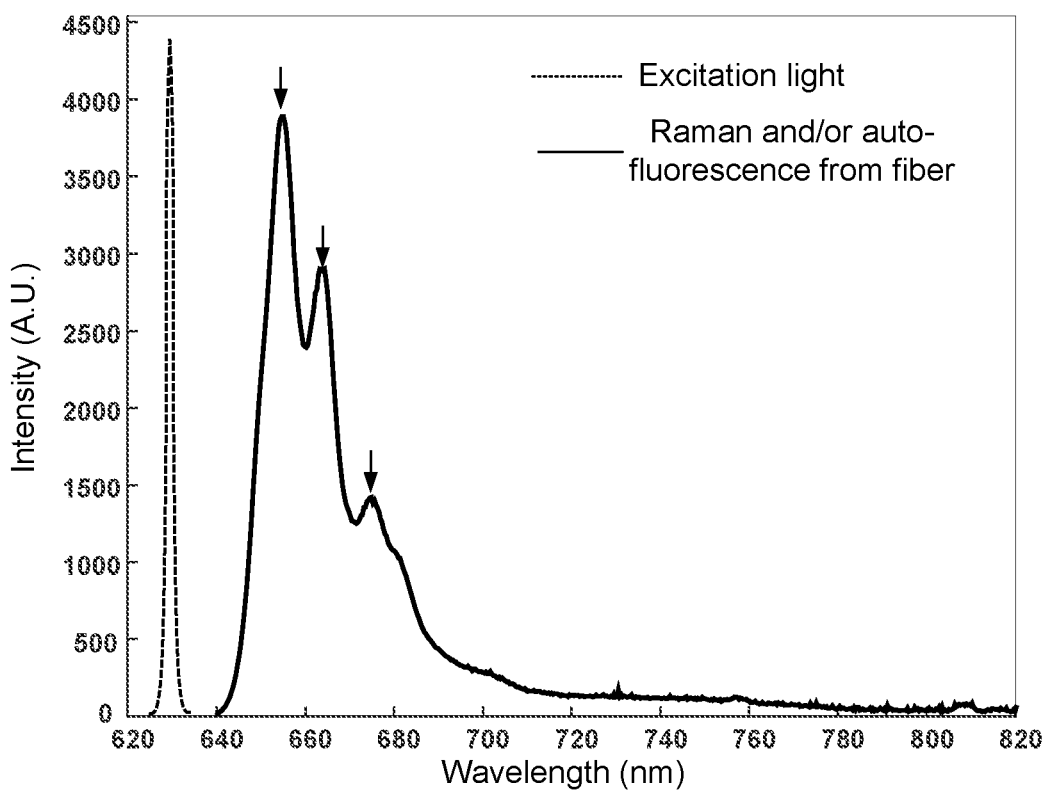
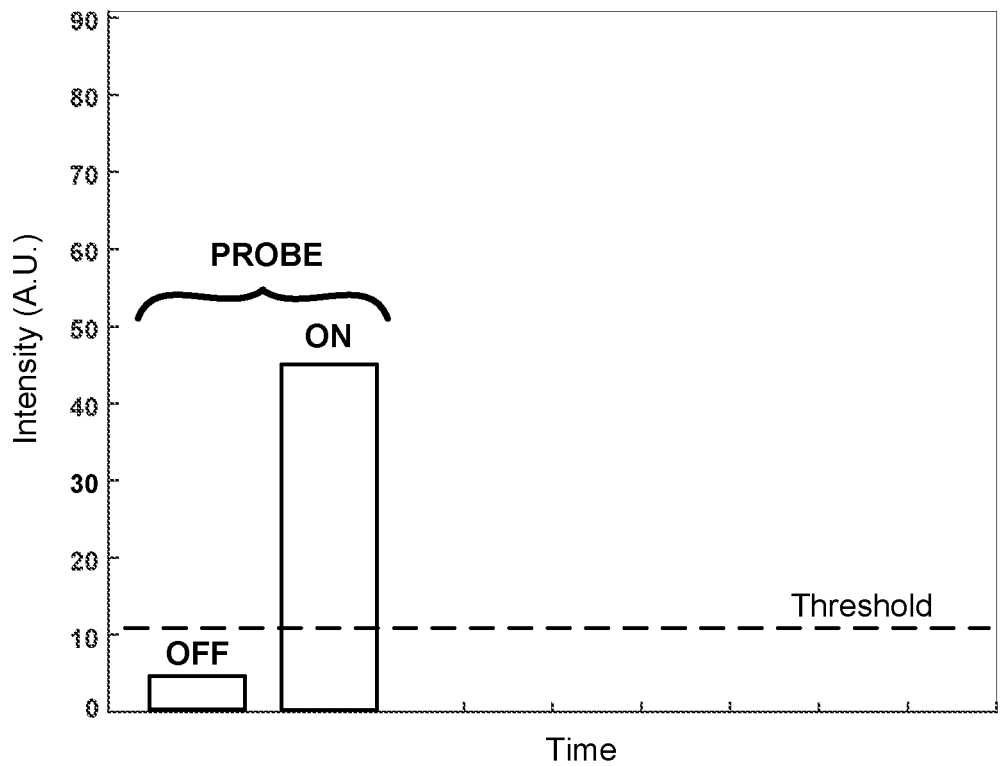
FIG. 5E

SYSTEM AND METHOD FOR DETECTING OPTICAL PROBE CONNECTION

CROSS-REFERENCE TO RELATED APPLICATIONS n/a

BACKGROUND

Field

Disclosure of present application relates generally to optical imaging, and in particular it relates to systems and methods for evaluating optical connection of fiber-based endoscopes or catheters to a console. The optical connection is evaluated using fiber-based Raman scattering or fluorescence signals such as spectra and intensity.

Related Art

Fiber optics-based probes, such as catheters and endoscopes, have been developed to access and image internal organs of humans and animals, and are now commonly used in various medical fields. For example in cardiology, optical coherence tomography (OCT), white light back-reflection, near infrared spectroscopy (NIRS) and fluorescence optical probes have been developed to obtain structural and/or molecular images of vessels and other bodily lumens with a catheter. An OCT catheter, which generally comprises a sheath, a coil and an optical probe, is navigated through a lumen, by manual or automatic control. In cardiology, the catheter is navigated to a coronary artery.

OCT and other fiber-based catheters are typically attachable to a console via a patient unit interface (PIU) so the catheter needs to be mechanically connected in a secure manner. In addition to a mechanical connection, the optical probe of the catheter needs to engage and align with other optical elements in the PIU to ensure proper transmission of light between the console and catheter. Therefore, evaluating the optical probe connection to the console is highly desirable in order to recognize the connection status thereof before using the catheter in a patient. In this manner, when an unexpected misalignment or disconnection occurs, the console system is able to alert medical personnel of potential errors.

Conventional techniques for evaluating the connection of an optical probe typically include interferometry methods such as OFDR (Optical Frequency Domain Reflectometry) or return power loss analysis. OFDR is commonly used to detect fiber connections, insertion losses, fiber damages, etc., in the field of telecommunications (see, e.g., U.S. Pat. Nos. 6,009,220 and 5,625,450). Return power loss refers to a technique of measuring losses from the distal optical probe for evaluating fiber connections for spectroscopic catheter (see. e.g., U.S. Pat. No. 7,132,645). Other techniques for evaluating an endoscope's status prior to its use on a patient include the use of dedicated test equipment to determine if an endoscope is ready for use (U.S. Pat. No. 8,758,223) and performance of optical tests compared to previously established database of threshold values (U.S. Pat. No. 6,069,691).

In the interferometry methods, the catheter sheath and/or the distal end of the optical probe need to be detected to confirm the connections. However, each optical probe has different length so the frequency of the interferometer varies. In some cases, the detection fails due to out of system frequency range. To accommodate various types of catheter or endoscopes, the system becomes complicated to increase the frequency range. Also, objects placed near the catheter sheath affect the interferometry analysis due to bending or interference, which results in a loss of reliability of detections. In return power detection methods, back-reflection power at different interface stages is evaluated, but reflections are very weak or may undergo transmission loss (attenuation) so it is difficult to reliably detect optical probe connections. Further, the use of dedicated test equipment increases the cost and time necessary to evaluate the connection status of an endoscope. Moreover, comparing optical tests of an instrument to previously established thresholds limits the evaluation to only the values of previously established thresholds which are unique to each type or model of endoscope.

SUMMARY

The present patent application aims to improve on the above-described state of the art. According to an aspect of the present application, a system is able to evaluate the status of optical probe connections of a catheter or endoscope by detecting Raman scattering and/or auto-fluorescence signals from the optical probe itself. Since evaluation of connection is performed using Raman scattering and/or auto-fluorescence signals of the optical probe itself, the method disclosed herein is able to achieve reliable detection of optical probe connection even before the catheter is inserted in the patient. In addition, since Raman scattering and/or auto-fluorescence signals are obtained from the optical probe itself, the optical probe connection can be accurately evaluated regardless of the type or model of catheter or endoscope.

According to one aspect of the present invention, a catheter system includes an electronic console; a catheter having a proximal end attachable to the console and a distal end configured to house therein an optical probe; an optical fiber configured to transmit from the console to the optical probe excitation radiation of a first wavelength, and configured to return to the console an optical response signal having a second wavelength longer than the first wavelength; a detector configured to detect intensity of the optical response signal; and a processor configured to determine, based on the detected intensity of the optical response signal, whether the optical probe is properly connected to the console, wherein the optical response signal is generated by at least one of photon scattering and auto-fluorescence within the optical fiber itself in response to transmitting the excitation radiation therethrough.

According to another aspect, a method of determining optical connection of a catheter to an electronic console is disclosed. The catheter has a proximal end attachable to the console, a distal end configured to house therein an optical probe, and an optical fiber that extends from the distal end to the optical probe. The method comprises: connecting the proximal end of the catheter to the console; transmitting excitation radiation from an optical source to the optical probe through the optical fiber, and collecting an optical response signal having a wavelength longer than that of excitation radiation; detecting the intensity or wavelength of the optical response signal; and determining, based on the detected intensity or wavelength, whether the optical probe of the catheter is properly connected to the console. The optical response signal is generated by at least one of photon scattering and auto-fluorescence within the optical fiber itself in response to transmitting the excitation radiation therethrough.

According to a further aspect of the present invention, a multimodality system includes first and second modalities, a catheter, and a processor. According to a further aspect of the present invention, a multimodality system includes first and second modalities, a catheter, and a processor. The catheter has a proximal end attachable to a console, a distal end configured to house therein an optical probe, and an optical fiber that extends from the distal end to the optical probe. The catheter is configured to transmit therethrough first radiation from the first modality and second radiation from the second modality to irradiate a sample. In response to transmitting the first and/or second radiations therethrough, the optical fiber generates an optical signal response in the form of Raman scattering and/or a fluorescence signal generated within the optical fiber itself. One or more detectors are configured to detect the intensity or wavelength of the optical signal response generated by the fiber itself. The one or more detectors are also configured to detect interference patterns based on collected scattered light emitted from a region of interest of the sample in response to irradiating the sample with the first radiation of the first modality, and detect fluorescence intensity based on fluorescent light emitted from the region of interest in response to irradiating the sample with the second radiation of the second modality. The processor is configured to process the interference patterns and detected fluorescence intensity emitted from the sample to generate one or more images of the region of interest. The processor is further configured to determine, based on the detected intensity or wavelength of the optical response signal, whether the optical probe is properly connected to the console. In particular, in response to determining an status of connection of the optical probe to the console, the processor is configured to inform a user of the connection status to prevent unsafe irradiation or to ensure safe irradiation of the sample with the first radiation from the first modality and/or with the second radiation from the second modality. In one embodiment, the first modality is an OCT system and the second modality is a fluorescence subsystem.

Further features and advantageous effects of the invention will become apparent to those skilled in the art from the following description of exemplary embodiments with reference to the attached drawings.

BRIEF DESCRIPTION OF DRAWINGS

FIG. 3A illustrates a free space beam combiner as an exemplary implementation of free-space optics used for multi-modality optical connections in the fiber optic rotary joint (FORJ). FIG. 3B illustrates an exemplary implementation of a fiber collimator unit.

FIG. 5D illustrates a graph of exemplary spectra of excitation laser light, and Raman and/or auto fluorescence signal obtained from the optical probe fiber itself. FIG. 5E illustrates an exemplary graph of indicative of optical probe connection status as a function of detected Raman and/or auto fluorescence signal intensity being compared to a threshold level.

DETAILED DESCRIPTION

Figure 1:
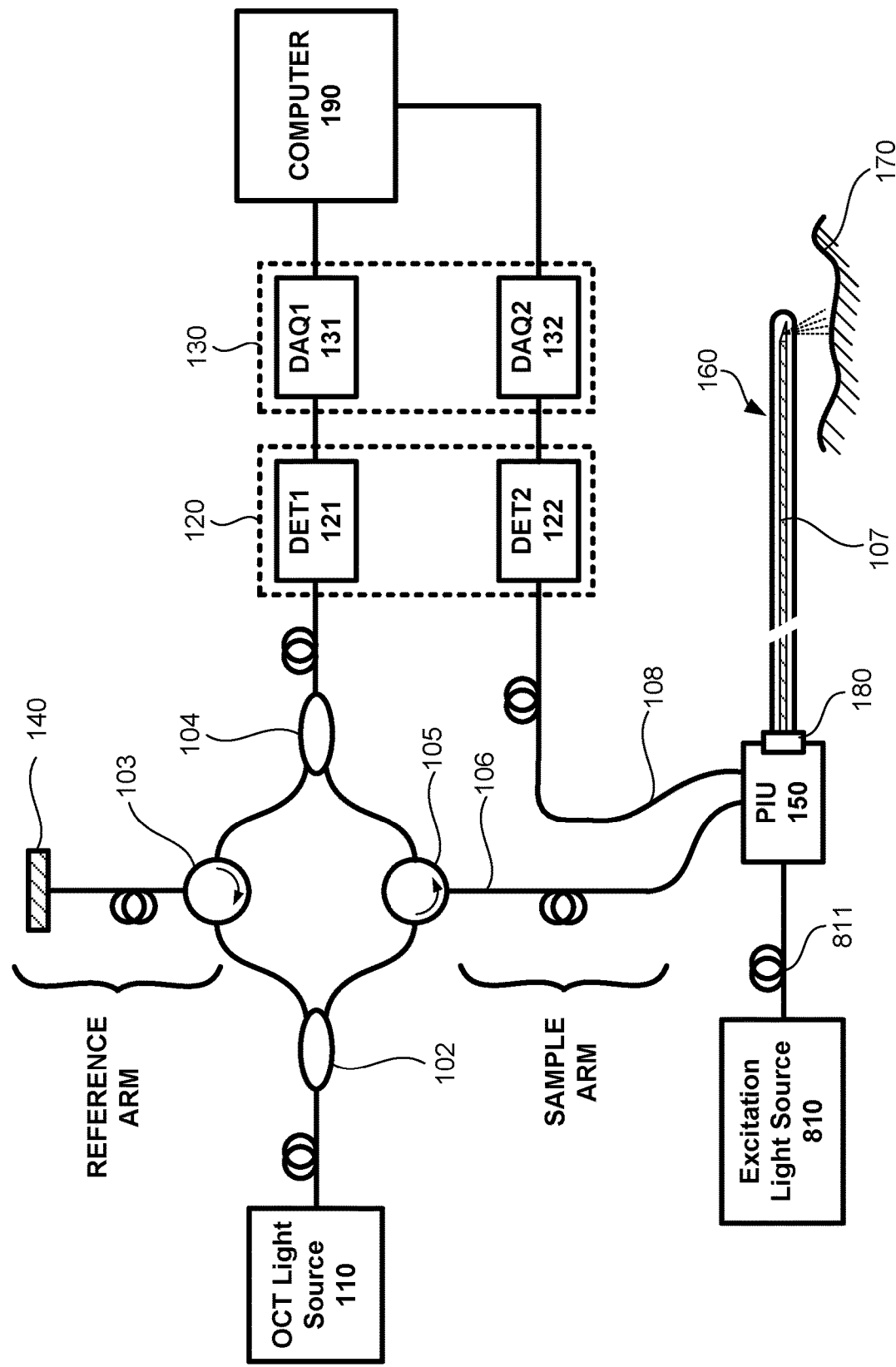
FIG. 1 illustrates an exemplary multimodality catheter system for imaging coronary arteries or other bodily lumens.

In the following description, reference is made to the accompanying drawings which are illustrations of exemplary embodiments in which the disclosed invention may be implemented and practiced. It is to be understood, however, that those skilled in the art may develop other structural and functional modifications without departing from the novelty and scope of the instant disclosure.

In referring to the description, specific details are set forth in order to provide a thorough understanding of the embodiments disclosed. Some aspects of the present disclosure may be implemented by a computer system that includes, in general, one or a plurality of processors for processing data including instructions, random access (volatile) memory (RAM) for storing data and instructions or programs, read-only (non-volatile) memory (ROM) for storing static information and instructions, a data storage devices such as a magnetic or optical disk and disk drive for storing information and instructions, an optional user output device such as a display device (e.g., a LCD or OLED monitor) for displaying information to a user, an optional user input device including alphanumeric and function keys (e.g., a keyboard or touchscreen) for communicating information and command selections to the processor, and an optional user input device such as a pointing device (e.g., a mouse) for communicating user input information and command selections to the processor.

In the present application, the described embodiments may be implemented as an apparatus, a method, or non-transitory computer-readable medium product storing thereon one or more programs. Accordingly, some implementations may take the form of an entirely hardware embodiment, an entirely software embodiment (including firmware, resident software, micro-code, etc.), or an embodiment combining software and hardware aspects that may all generally be referred herein as a "module", a "unit", or a "system". Some embodiments described below with reference to flowchart illustrations and/or block diagrams may be implemented by computer-executable programed instructions. The computer program instructions may be stored in computer-readable media that when executed by a computer or other programmable data processing apparatus causes the computer or processing apparatus or processor to function in a particular manner, such that the instructions stored in the computer-readable media constitute an article of manufacture including instructions and processes which implement the function/act/step specified in the flowchart and/or block diagram.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims may be drafted to exclude any optional element; such claims may use exclusive terminology as "solely," "only" and the like in connection with the recitation of claim elements, or it may use of a "negative" limitation.

As used herein the term "endoscope" refers to a rigid or flexible medical instrument which uses light guided by an optical probe to look inside a body cavity or organ. A medical procedure, in which an endoscope is inserted through a natural opening, is called an endoscopy. Specialized endoscopes are generally named for how or where the endoscope is intended to be used, such as in the mouth during a bronchoscopy, or the rectum for a sigmoidoscopy. Other examples include the cystoscope (bladder), nephroscope (kidney), bronchoscope (bronchi), laryngoscope (larynx), otoscope (ear), arthroscope (joint), laparoscope (abdomen), and gastrointestinal endoscopes. The term "catheter" generally refers to a flexible and thin tubular instrument made of medical grade material designed to be inserted through a narrow opening into a body cavity to perform a broad range of medical functions. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe.

In the present disclosure, the terms "optical fiber", "fiber optic", or simply "fiber" refers to an elongated, flexible, light conducting conduit capable of conducting light from one end to another due to the effect known as total internal reflection. The term "fiber" may refer to one or more light conducting fibers. A fiber has a transparent, homogenous core, where the light is guided, and the core is surrounded by a homogenous cladding. The refraction index of the core is larger than the refraction index of the cladding. Depending on design choice some fibers can have multiple claddings surrounding the core.

As used herein the term "optical coherence tomography" or its acronym "OCT" refers to an interferometric, optical tomographic imaging technique offering millimeter penetration (approximately 2-3 mm in tissue) with micrometer-scale axial and lateral resolution. The term "Raman spectroscopy" refers to an optical technique that reveals the specific molecular content of a sample by collecting inelastically scattered light based on the principles of Raman scattering. As photons propagate through a medium, they undergo both absorptive and scattering events. In absorption, the energy of the photons is completely transferred to the material, allowing either heat transfer (internal conversion) or re-emission phenomena such as fluorescence and phosphorescence to occur. Scattering is normally an inelastic process, in which the incident photons retain their energy. In Raman scattering, the photons either donate or acquire energy from the medium, on a molecular level. In contrast to fluorescence, where the energy transfers are on the order of the electronic bandgaps, the energy transfers associated with Raman scattering are on the order of the vibrational modes of the molecule. These vibrational modes are molecularly specific, giving every molecule a unique Raman spectral signature. Raman spectra are plotted as a function of frequency shift ($1/\lambda$) in units of wavenumber ($cm^{-1}$). Fluorescence relates to substances which absorb light at one wavelength, undergo internal conversion, and then re-emit light at a longer wavelength as a result of electronic transitions. As an example, a "highlighter" felt-tip marker appears to "glow" green as it absorbs blue and ultraviolet light then emits it as green. Fluorescence provides a powerful technique for chemical monitoring.

Exemplary embodiments are described below in more detail with reference to the several drawings where like reference numerals refer to like parts.

<Multi-Modality Catheter System>

According to a first embodiment, a multi-modality catheter system includes an OCT system and a fluorescence subsystem which share a common optical probe to illuminate and collect light from a sample. The catheter comprises a sheath, a coil, a protector and an optical probe. The optical probe comprises an optical fiber connector, an optical fiber and a distal optics assembly. The OCT system comprises an interferometer and the catheter arranged on the sample arm of the interferometer. The catheter having the optical probe, which includes a focusing element (GRIN or ball lens) attached at the distal end of an optical fiber with at least 2 dads (also known as double clad fiber or DCF), is attachable and detachable from the sample arm. The fluorescence subsystem comprises the same catheter and an excitation light source separate from the interferometer.

<OCT System>

More specifically, FIG. 1 illustrates an exemplary multi-modality catheter system 100 including an interferometric OCT modality and a fluorescence spectroscopy modality that can be applied as an intravascular OCT/fluorescence catheter system for imaging of coronary or carotid arteries.

Alternatively, the multi-modality system 100 can be applied as an endoscopic system (endoscope) for imaging other bodily lumens. As depicted in FIG. 1, the system 100 includes an OCT modality comprised of an interferometer having a sample arm (SAMPLE ARM) and a reference arm (REFERENCE ARM), an OCT light source 110 (first light source), a detector unit 120, a data acquisition unit 130, and a computer 190. The sample arm of the interferometer includes a patient interface unit (PIU) 150 connected to a catheter 160 via a catheter connector 180. The reference arm includes a reflector 140. The interferometer can be of any interferometer configuration, including a Michelson interferometer implemented with optical fibers. In addition, the system 100 includes a fluorescence subsystem (fluorescence modality) comprised of an excitation light source 810 (second light source) also connected to the same catheter 160 via an optical fiber 811, and connected to computer 190 via the PIU 150. In one embodiment, the system 100 uses a swept-source laser (wavelength 1310 nm+/−50 nm) as the OCT light source 110, and a HeNe laser (wavelength 633 nm) as the excitation light source 810 for the fluorescence subsystem.

The catheter 160 comprises a sheath, a coil, a tubular protector, and an optical fiber 107 extending from a proximal end to a distal end along an axis thereof. In one embodiment, the fiber 107 is double clad fiber (DCF). At the proximal end, the catheter is configured to be detachably connected to the PIU 150 via the catheter connector 180, and the distal end of the catheter 160 is configured to house therein a distal optics assembly (an optical probe) which includes, for example, a ball lens attached at the distal end of the fiber. The distal optics assembly (optical probe) may alternatively include combination of a graded index (GRIN) lens and a refractive element (e.g., grating) attached at the distal end of the fiber 107. In a further alternative embodiment, the optical probe may be formed by polishing the distal end of the optical fiber 107 at a predetermined angle and forming thereon a refractive element (grating) by nanoimprint lithography techniques, as described in publication US 2016/0349417. The optical probe can be configured for side-view imaging or for front-view imaging depending on design choice and optical/mechanical constraints of the desired application.

In operation, light from the light source 110 is guided through the sample arm to a sample 170, and through the reference arm to the reflector 140. Light retuning from the sample 170 and reflector 140 undergo interference at a beam combiner 104 to thereby generate OCT interference patterns. Specifically, light from the light source no is divided by a splitter 102 (fiber splitter or beam splitter) into a sample beam and a reference beam which are respectively guided to the sample arm and the reference arm via respective optical fibers (not labeled). In the sample arm, the sample beam enters a circulator 105, passes to a fiber 106 (e.g., a single mode fiber), and thenceforth the sample beam is delivered to the catheter 160 via the PIU 150. The catheter 160 is connected at its proximal end thereof to the PIU 150 via the connector 180, and the PIU 150 is also connected to computer 190. Under control of computer 190, the PIU 150 directs the sample beam to irradiate the sample 170 in a scanning manner. Light of the sample beam reflected and/or scattered by the sample 170 is collected by the distal optics assembly (optical probe) arranged at the distal end of the catheter 160, and the collected light is transmitted back to the PIU 150 through either the same fiber 107 or other collection fibers (not shown). From the PIU 150, the collected light is guided by fiber 106 back to the circulator 105.

In turn, a beam combiner arranged in the PIU 150 forwards the collected light to the circulator 105 which then guides the collected light of the sample beam to the combiner 104.

At the same time, in the reference arm, light of the reference beam enters a circulator 103 and is delivered to the reflector 140 via a non-labeled optical fiber. In the case of Time Domain OCT (TD OCT) imaging, the reflector 140 may be implemented as a scanning mirror. And, in the case of Frequency Domain OCT (FD-OCT) imaging, the reflector 140 may be implemented as a stationary mirror. Light of the reference beam reflected from the reflector 140 passes through the circulator 103, and is also guided by the circulator 103 to the combiner 104. In this manner, the sample and reference beams are combined at the combiner 104 and interference patters formed by the sample and reference beams are detected by one or more first detectors 121 (OCT detectors) to generate interference signals according to OCT principles.

Here, it is noted that a fiber optic circulator (e.g., circulator 103 or 105 in FIG. 1) is a passive, polarization-independent, three-port device that acts as a signal router. Light from a first fiber is input to the circulator via a first port and directed to a second fiber via a second port. Light returning through the second fiber is redirected to a third fiber via a third port with virtually no losses. That is, light input into the first port is not directly coupled into the third port fiber, and light input into the second port is not coupled at all into the first port fiber. Therefore, the optical circulator (103 and 105) enables a balanced output of the sample and reference beams to obtain accurate interference patterns from the OCT interferometer. However, other equivalent optical arrangements (e.g., combination of mirrors and beam splitters) can be used instead of optical circulators.

The output of the interferometer (interference patterns) is detected by the detector 121 (first detector). The first detector 121 can be implemented by multiple photodiodes (e.g., an array of photodiodes), a photo multiplier tube (PMT), a multi-array of cameras or other similar interference pattern detecting device. The signals output from the first detector 121 are pre-processed by a first data acquisition electronics card (DAQ1) 131. The DAQ1 digitizes the OCT signals and transfers the OCT data to computer 190. It is noted that data acquisition (DAQ) more generally refers to the process of measuring an electrical or physical signal such as voltage, current, temperature, pressure, or sound with a computer. A DAQ system may include sensors, measurement hardware, and executable software. In the present disclosure a DAQ unit (module or system) refers to the hardware and/or software necessary to measure the signals from the OCT system and fluorescence subsystem with computer 190. In this manner, computer 190 performs signal processing of the OCT signals output from detector 121 to generate OCT images. Interference patterns formed by interference of the sample and reference beams are generated only when the path length of the sample arm matches the path length of the reference arm within the coherence length of the light source 110.

<Fluorescence Subsystem>

In the fluorescence modality (fluorescence subsystem), the excitation light source 810 (second light source) emits excitation light with a wavelength of 633 nm. The excitation light is guided first to the PIU 150 through a fiber 811, and the beam combiner in PIU 150 transmits the excitation light to the distal optics of catheter 160 via the fiber 107. In this manner, the catheter 160 also irradiates the sample 170 with excitation light having a wavelength different from that of the OCT light. The sample 170 emits auto-fluorescence (NIRAF signal) or fluorescence (NIRF signal) with broadband wavelengths of about 633 to 900 nm, in response to being irradiated by the excitation light. The auto-fluorescence (or fluorescence) light is collected by the distal optics of the catheter 160 and delivered to a fluorescence detector 122 (DET2) via an optical fiber 108 which is connected to the PIU 150. The fluorescence signal (fluorescence intensity signal) output from detector 122 is digitized by a data acquisition electronics card 132 (DAQ2), and the digitized fluorescence data is transmitted to computer 190 for image processing.

The multi-modality catheter system 100 is illustrated in FIG. 1 as being constituted of separate elements for ease of illustration. However, a console containing the different elements (e.g., interferometer, PIU, computer, etc.) and having connection ports for electrically coupling medical instruments such as a catheter is generally used when performing a medical procedure. An example of a console having connection ports for electrically coupling equipment thereto for performing a medical procedure is described in publication US 20170333013.

<Patient Unit Interface (PIU)>

Figure 2A:
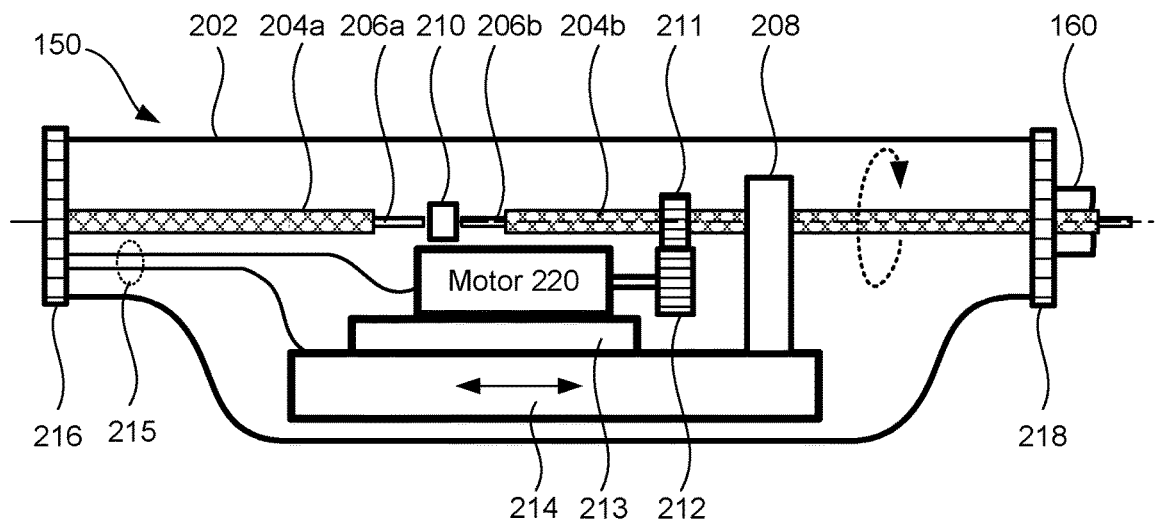
FIG. 2A schematically shows one exemplary implementation of relevant parts of a patient interface unit (PIU).

FIG. 2A schematically shows one exemplary implementation of relevant parts of a patient interface unit (PIU) 150 which is detachably connected to the proximal end of catheter 160 (shown in FIG. 1). As shown in FIG. 2A, the PIU 150 is encased in an outer housing 202, which serves as a housing for mechanical, electronic, and optical components useful for control of the optical probe of catheter 160. Included in the housing 202 of PIU 150 is a fiber optic rotary joint (FORJ) comprised of a free-space optical connector 210, a rotational motor 220, a motorized translation stage 214. At one end, the PIU 150 is provided with an optical/electrical connector 216, and at the other end thereof the PIU 150 is provided with a catheter connector 218. The connector 216 serves to connect one or more fibers 206a encased in a protective jacket 204a and electronic wiring connections 215 of the PIU 150 to an operating console which includes the computer 190. The console connects to the PIU via a cable bundle. A first end of a double clad fiber (DCF) 206b encased in a protective jacket 204b are part of the free-space connector 210 and the other end of DCF 206b is connected to the catheter 160 via the connector 218.

The motor 220 and motorized translation stage 214 provide rotational and translational torque for actuation of the movable components of catheter 160. Motor 220 drives a non-labeled shaft to rotate a first gear 212 which transfers rotational torque to a second gear 211. The motor 220 is mechanically fixed to a base plate 513. In addition, a motorized translation stage 214 is also fixed to the base plate 213. The motorized translation stage 214 serves to provide translational torque for controlling linear movement (insertion into a lumen or pullback) of the movable components within catheter 160. A support beam 208 provides support and directional control for translational movement of the movable components within catheter 160. In other words, support beam 208 serves as a linear guide for translational movement. The motorized translation stage 214 is also used for providing translational torque during a pullback operation. The connector 518 is a catheter connector to be mechanically attachable to and detachable from the catheter 160. Although a single fiber 206a and a single DCF 206b are shown in FIG. 2A, more than one fiber can be used to transmit the light from OCT light source 110 and light from the excitation light source 810 to the PIU 150.

Figure 2B:
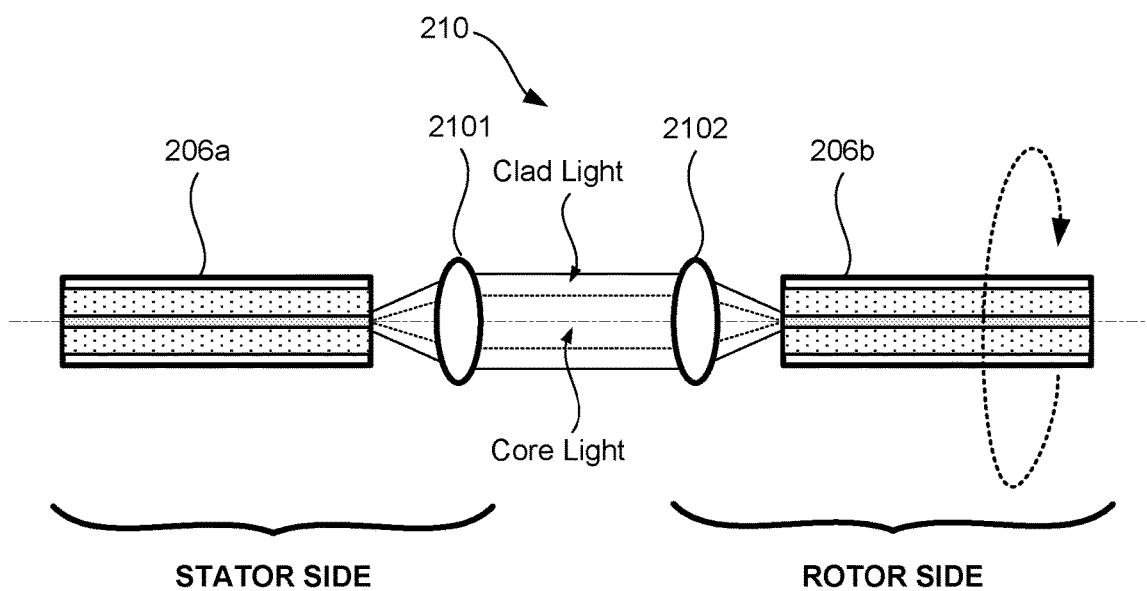
FIG. 2B shows an exemplary implementation of free-space optics used as a one-to-one optical connection in a fiber optic rotary joint (FORJ).

FIG. 2B shows a simplified view of an exemplary implementation of the free-space optical connector 210 which is part of the FORJ. The free-space optical connector 210 includes free space optics such as a pair of lenses 2101 and 2102. The FORJ allows uninterrupted transmission of optical radiation from one or both of the light sources (110 and 810) to the catheter 160 while rotating the double clad fiber 206b on the rotor side (right side). The FORJ has a free space optical beam coupler to separate rotor and stator sides. The rotor and stator sides each includes at least a fiber and a lens to ensure the light is transmitted as a collimated beam. The rotor side is connected to the catheter 160, and the stator side is connected to the optical sub-systems within the PIU 150. The rotational motor 220 delivers the rotational torque to the rotor or rotational side. It should be understood from FIG. 2B that the lens 2101 needs not be separated from the fiber 206a, and similarly lens 2102 needs not be separated from the fiber 206b. As long as a collimated beam is transferred from the stator side to the rotor side and vice versa, the lenses 2101 and 2102 can be arranged at any position between fiber 206a and fiber 206b. Indeed, for ease and convenience of fabrication, the lenses 2101 and 2102 can be fused or glued with epoxy or resin at the respective tips of fiber 206a and fiber 206b.

<Free-space Beam Combiner>

FIG. 3A illustrates an exemplary embodiment of a free-space beam combiner 300 which can be implemented within the free-space optical connector 210. The beam combiner 300 shown in FIG. 3A is a more detailed representation of the free-space optical connector 210 shown in FIG. 2B. The free-space beam combiner 300 serves to separate the rotor side from the stator side of the FORJ. The rotor side is connected to the optical probe through catheter connector 218 (shown in FIG. 2A), and the stator side is connected to the optical sub-systems.

In FIG. 3A, the free-space beam combiner 300 includes a plurality of fiber collimator units, which function as an OCT light channel 302, a return optical signal channel 304, an excitation light channel 306, on the stator side, and an optical probe channel 308, on the rotor side. The free-space beam combiner 300 also includes a plurality of dichroic beam splitters (dichroic filters) 310A and 310B, one or more mirrors 312, and one or more optical filters 320. As shown in FIG. 3A, the OCT channel 302 transmits OCT light in both directions (illumination and collection). The excitation light channel 306 transmits excitation light in only one direction (from the console to the optical probe). The optical probe channel 308 transmits OCT light and excitation light to the optical probe (and through the catheter to the sample); the optical probe channel 308 also serves to transmit light from the optical probe back to the detectors. And, in turn, the return optical signal channel 304 transmits a response signal returned from the optical probe channel towards the console.

OCT light from the OCT light source 110 travels through OCT channel 302, dichroic mirror 310A, and optical probe channel 308 to irradiate a non-illustrated sample. The excitation light channel 306 transmits light from the excitation light source 810 to the sample. To that end, an excitation light beam travels through excitation light channel 306, is guided by mirror 312 towards the dichroic beam splitter 310B through which the excitation light travels uninterrupted to be redirected by dichroic 310A towards the optical probe channel 308. As explained in more detail elsewhere in this specification, the excitation light transmitted through the optical probe channel 308 causes the optical probe to generate a response optical signal in the form of auto-fluorescence and/or Raman scattering. The dichroic beam splitters 310A and 310B serve to separate and guide the lights of different wavelengths including OCT light, excitation light, and a return optical signal (Raman scattering and auto-fluorescence) generated by the probe itself. The one or more optical filters 320, which can be low-pass filters or band-pass filters, are arranged in front of the return optical signal channel 304 to allow the Raman scattering and/or auto-fluorescence signals coming back from the optical probe to travel therethrough and to prevent the excitation light from returning to detector because of the need to minimize excitation light noises at the fluorescence detector. The cut-off wavelength of the optical filter 320 (low-pass or band-pass) is selected from around 645 to 700 nm.

<Optical Probe Connection>

As shown in FIG. 3A, one end of the fiber collimator unit of channel 308 connects to (and is part of) the free-space beam combiner 300 and the other end (second end) of the collimator unit connects to the optical probe. Since the optical probe comprises a fiber connector at the proximal end thereof, and that fiber connector of the probe is connected to the fiber collimator unit of channel 308, it is important to confirm the optical alignment of the fiber collimator unit of channel 308 with the fiber connector of the optical probe. Most fiber optic connectors are plugs or so-called male connectors with a protruding ferrule that holds a fiber in the center therein and aligns the fiber for mating two fibers or for connecting the fiber to a light source or detector. Fiber connectors usually use a mating adapter portion to mate two connector ferrules, where the mating adapter fits a securing mechanism of the connectors (bayonet, screw-on or snap-in) to lock the connected portions. The ferrule design can be made specific for connecting to a mating adapter or for connecting directly to light sources like LEDs and VCSELs, or to detectors like PIN photodiodes. In the field of medical imaging with fiber-optic based catheters, the design of optical catheter connectors must meet the requirements of sterile usage, reliable performance, ease of assembly, and intuitive connection and disconnection procedures. To that end, the catheter connector should provide a clear indication that proper engagement between the catheter connector and the PIU is achieved.

In the present application, as shown in FIG. 1, a catheter connector 180 connects the fiber 107 of catheter 160 to the PIU 150. In FIG. 3A, a rotatable fiber collimator unit 380 for the optical probe channel 308 is configured to engage and disengage with fiber 107 of catheter 160. FIG. 3B shows the fiber collimator unit 380 in more detail. The fiber collimator unit 380 includes a sleeve 382 and a ferrule 384. The ferrule 384 holds in the center thereof a core 1071 of fiber 107. The fiber collimator unit 380 connects and aligns on one side the fiber 107 and on the other side a lens 381 so that light is transmitted reliably from the stator to the rotor and vice versa. The lens 381 is attached to the sleeve 382 by an adhesive material 385, such as epoxy or resin material. The fiber collimator unit 380 may be implemented as a bayonet style connector requiring rotation of the connector about the axis of the optic fiber 107 to engage the optical probe. Alternatively, a fiber connector may be implemented at the second end the fiber collimator unit 380 as a latching connector, a plug-to-jack connector, a snap-in connector, and the like. In this manner, the fiber connector at the second end of fiber collimator unit 380 serves to engage and disengage with the fiber connector of catheter 160. The fiber collimator units corresponding to channels 302, 304 and 306 have a similar structure to the fiber collimator unit 380 except that those fiber collimator units are not rotatable.

<Optical Probe>

Figure 4A:
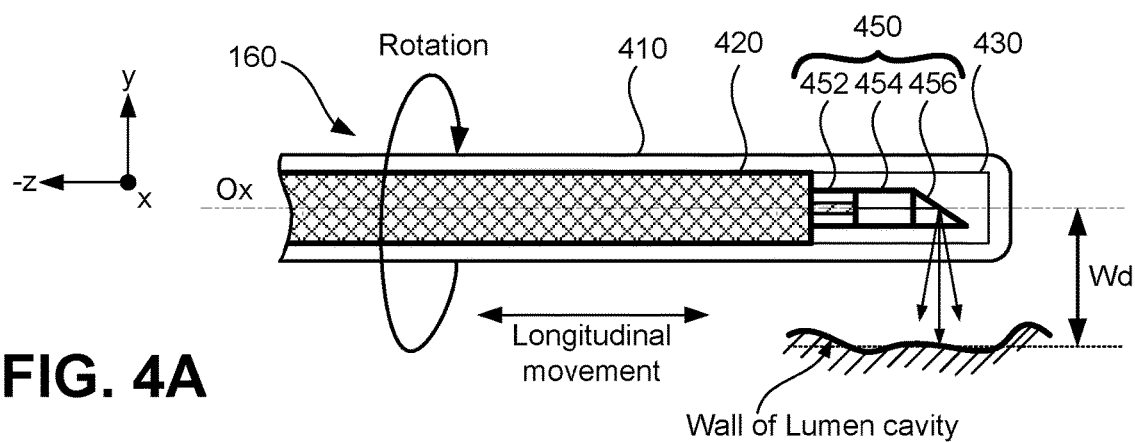
FIG. 4A illustrates an example of an optical probe arranged at the distal end of the catheter with exemplary light rays incident on a sample.

FIG. 4A illustrates an exemplary representation of a distal end (optical probe) of catheter 160. As illustrated in FIG. 4A, catheter 160 comprises a transparent sheath 410, a coil 420, a transparent protector 430 and an optical probe 450. The optical probe 450 arranged at the distal end of the catheter 160 includes a double clad fiber 452, a lens 454 (e.g., a GRIN lens or a ball lens), and a reflecting and/or diffracting element (e.g., prism) 456. The catheter 160 is connected at the proximal end thereof to the PIU 150 (as shown in FIG. 1) via a connector 180. The coil 420 shown in FIG. 4A delivers rotational torque from the proximal end to the distal end of the catheter 160. As explained above, the rotational torque is provided by rotational motor 220 located in the PIU 150. At the distal end of the catheter 160, a reflecting surface or diffracting surface of diffracting element 456 (e.g., a mirror, a prism, or a grating) deflects the illumination light (sample beam) in a transverse direction toward the sample (wall of the lumen cavity). As shown in FIG. 4A, the optical probe 450 is configured for side-view imaging, where the illumination light incident on the sample surface travels along a line transverse to the catheter's axis Ox. Depending on the design of the optical probe, the illumination light may also be guided in a direction substantially parallel to the longitudinal axis Ox for front-view imaging.

The optical probe 450 is rigidly attached to the inner surface of coil 420, so that the distal end (tip) of double clad fiber 452 spins (rotates) along with the optical probe 450 to obtain an omnidirectional view of the inner surface of hollow organs (lumens), such as vessels being imaged. At the proximal end of the optical probe 450, the double clad fiber 452 is connected with the PIU 150 via a non-illustrated fiber connector. The double clad fiber 452 is used to deliver and collect OCT light through the core, and to collect backscattered and fluorescent light from the sample through the cladding, as explained more in detail below. The lens 454 is used for focusing and collecting light to and/or from the sample, by disposing the catheter 160 at a working distance (Wd) from the sample. The intensity of backscattered light transmitted through the cladding of double clad fiber 452 is relatively higher than the intensity of backscattered light collected through the core because the size of the core is much smaller than the cladding.

Figure 4B:
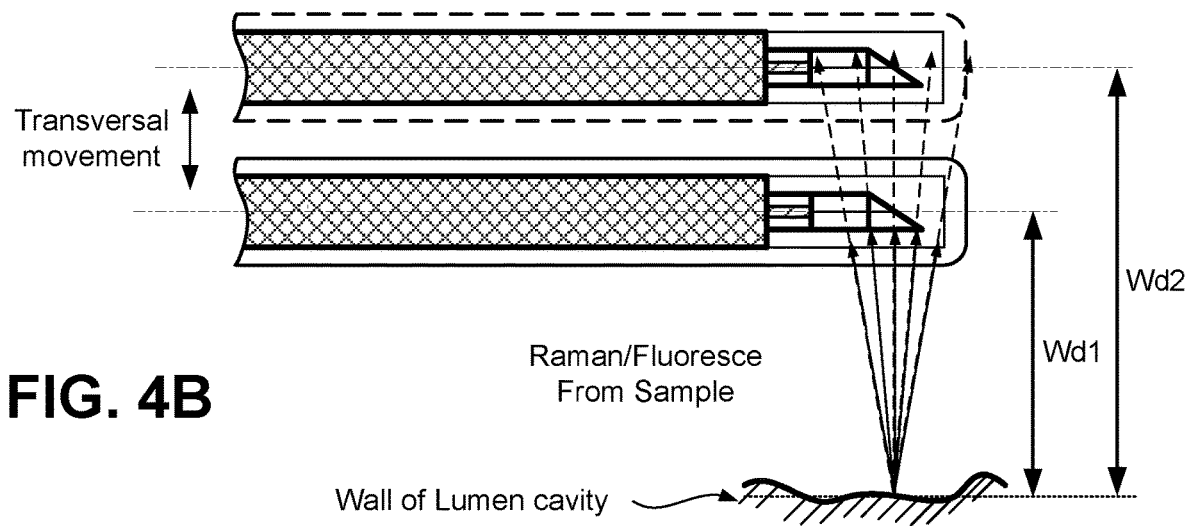
FIG. 4B shows exemplary movement of the distal end of the catheter with respect to the sample and exemplary light rays scattered by the sample and collected by the optical probe.

FIG. 4B illustrates the distal optics of catheter 160 imaging the wall of a lumen cavity (a blood vessel) at variable distances between the catheter and the sample surface (vessel wall). As illustrated in FIG. 4B, fluorescence and backscattered light can be collected at a plurality of working distances (Wd1, Wd2, Wd3 . . . ). Therefore, the detected fluorescence intensity can be detected as a function of the distance between catheter and the lumen cavity wall (wall of blood vessel sample). That is, the detected intensity of collected fluorescence decreases with increased distance from catheter to sample (vessel wall).

<Fiber-Based Raman Scattering and Fluorescence Optical Signal Response>

Fiber-optic catheter configurations that combine Raman spectroscopy with optical coherence tomography (OCT) have been proposed by previous patent applications and academic publications; see, for example, Motz et al., "Optical Fiber Probe for Biomedical Raman Spectroscopy", Applied Optics Vol. 43, No. 3, 20 Jan. 2004, US 2008/0304074 (Brennan), and US 2012/0176613 (Marple et al.). In these and other publications, it has been found that the collection of Raman spectra from biological tissue, i.e., Raman spectra in the wavenumber region from about 400 to 2,000 $cm^{-1}$, through optical fibers is complicated by the Raman signal (background signal) from the fiber itself. The intensity of the fiber's background signal is equal to, or even larger than, the Raman scattering signal from the tissue being examined. The background signal of the fiber is composed of Raman scattering from the fused-silica core and/or cladding, and fluorescence from impurities and dopants used to produce the fiber core and/or cladding, which are distributed along the entire length of the fiber (approximately 1-3 meters) typically used in a catheter.

Ma et al., in "Fiber Raman background study and its application in setting up optical fiber Raman probes", Appl. Opt. 1996, found that (a) all Raman background spectra of fused-silica fibers are very similar regardless of the difference in cladding and buffer materials; and that the overall background intensity increases with the fiber numerical aperture but has no obvious relation with the core diameter. Therefore, in catheters that combine Raman spectroscopy with optical coherence tomography, it has been necessary the use of a band-pass filter at the distal end of the illumination fiber(s) to remove the silica Raman bands arising from the fiber itself before illuminating a sample, and the use of a long-pass filter disposed before the collection fiber(s) so that only the sample-based Raman signal enters the collection fiber(s). In other words, in order to collect Raman spectra from a sample, it has been conventionally necessary to incorporate complex optics and filters on the distal end of optical catheters. This makes the catheters not only more complicated to fabricate, but also more expensive and less flexible.

The inventor herein proposes a fiber-optic based catheter system that is able to evaluate the status of the optical probe connection by detecting Raman and/or auto-fluorescence spectra signals generated from the optical probe itself. This proposed method is able to achieve reliable detection of optical probes regardless of the differences in the structure of the optical probes or the type of catheter being used. This is contrary to conventional technology where optical probes are typically designed with filtering techniques designed to remove the majority of the fiber-based Raman background signal. Referring back to FIGS. 1, 3A and 4A, according to the present invention, detection and evaluation of optical probe connection is achieved by controlling the fluorescence sub-system to emit excitation light for a short period of time and then detecting the Raman and/or auto-fluorescence spectra generated from the fiber 107 of the optical probe itself. Advantageously, by using the fluorescence subsystem, the detection and evaluation of optical probe connection can be performed without requiring additional hardware, without using complicated optics (filtering) at the distal end of the catheter, and without putting the catheter in contact with a patient.

According to at least one embodiment of the present invention, e.g., as illustrated in FIG. 1, the excitation light emitted from excitation source 810 goes through the optical fiber 107 to the optical probe of catheter 160. Raman scattering and/or auto-fluorescence light are spontaneously generated from the fiber 107 itself, in response to the fiber 107 being irradiated with the excitation light emitted from excitation source 810. Details of spontaneous Raman scattering and/or auto-fluorescence generation from optical fibers can be found, for example, in technical documents disclosed by Walrafen et al., "Raman Spectral Characterization of Pure and Doped Fused Silica Optical Fibers", Applied Spectroscopy, Volume 29, Number 4, 1975, pages 337-344, and Motz et al., "Optical Fiber Probe for Biomedical Raman Spectroscopy", Applied Optics Vol. 43, No. 3, 20 Jan. 2004. In the present disclosure, significant consideration is given to optimizing throughput and maximizing collection efficiency of the fiber-based Raman scattering and fluorescence signals. As it is known to those skilled in the art, the Raman effect allows for only about 1 of every 109 excitation photons to produce a Raman signal. For this reason, it is desirable to collect the fiber-based scattering signal with high signal-to-noise ratio.

In the system 100 of FIG. 1, the generated Raman scattering and/or auto-fluorescence light are delivered back to the PIU 150, e.g., due to reflection from optical interfaces at the distal end of the fiber. More specifically, as illustrated in FIG. 4A, the optical probe 450 shows at least one interface between fiber 452 and lens 454, and also an interface between lens 454 and diffracting element 456. These interfaces can cause the return the spontaneously generated Raman and/or auto-fluorescence from the optical probe back towards the fluorescence detector 122. The Raman scattering and/or auto-fluorescence signal is transmitted to the fluorescence detector 122 via the free-space beam combiner 300 in the PIU 150. Specifically, as illustrated in FIG. 3A, the beam combiner 300 guides the light from the optical probe channel 308 to the return signal channel 304, by passing the generated Raman scattering and/or auto-fluorescence signal through the optical filters 320, such as a long-pass and/or bandpass filter. Then, the Raman spectrum and/or the fluorescence signal can be detected with a spectrometer and/or the fluorescence detector 122.

Figure 5A:
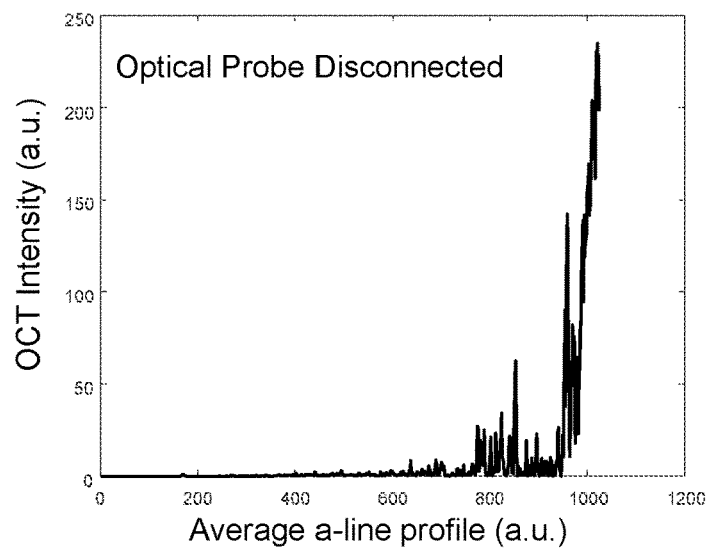
FIGS. 5A through 5C graphically illustrate a comparative example of assessing optical probe connection based on detected OCT signals.
Figure 5B:
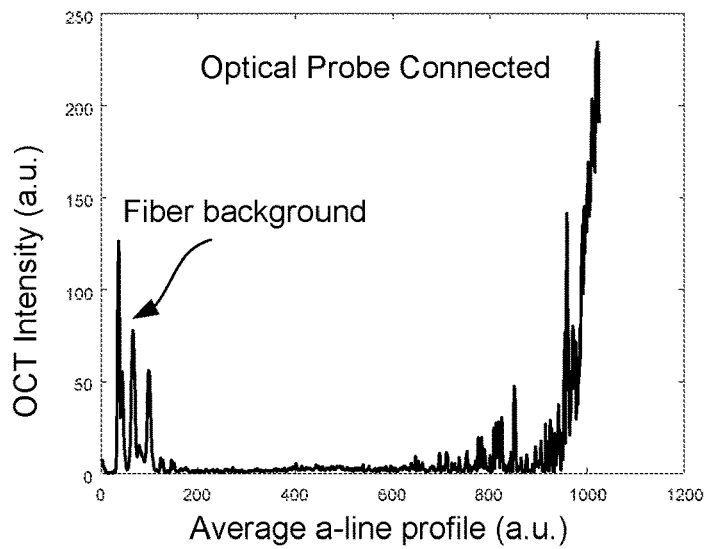
Figure 5C:
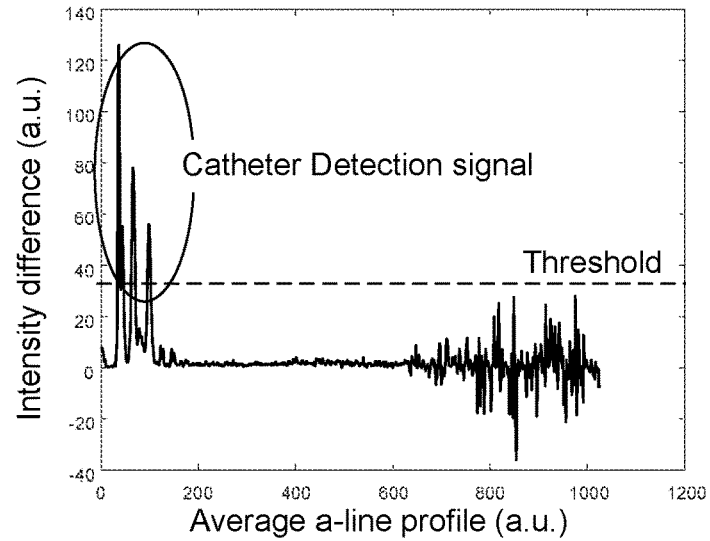

In the system 100 shown in FIG. 1, it is also possible to assess the optical connection of the catheter 160 based on OCT signals detected from a sample. FIGS. 5A through 5C graphically illustrate a comparative example of evaluating the optical probe connection based on OCT signal intensity using the system 100 (shown in FIG. 1). To obtain an OCT signal as shown in FIGS. 5A-5C, the catheter 160 would have to be mechanically connected with PIU 150, and then placed near (inserted into) a sample 170 (e.g., a bodily lumen). As shown in FIG. 5A, when the optical probe is optically disconnected from the PIU 150 (e.g., when the fiber 107 is misaligned), even if the OCT light source no is activated, the average a-line profile shows only a signal intensity corresponding to the light source 110 (or system) thermal noise. That is, when the optical probe is disconnected, there is no sample-based or fiber-based signal. However, as shown in FIG. 5B, when the optical probe is connected to the PIU 150 and the light source 110 is activated, the average a-line profile has a signal intensity corresponding to the light source (or system) thermal noise and a signal corresponding to OCT signal returning from the sample 170. In addition, a fiber background signal (Raman scattering and/or auto-fluorescence spectra) generated from the optical probe fiber itself may be observed. Therefore, as shown in FIG. 5C, the signals obtained when the optical probe is disconnected and when the optical probe is connected can be used to obtain a signal indicative of whether the optical probe is connected or not. Specifically, FIG. 5C shows the intensity difference by combining (subtracting) the signals detected before and after the optical probe is connected to PIU 150. However, in order to preform the measurement shown in FIG. 5B, the catheter 160 must be in close contact with an actual subject (sample 170). In this case, since the fiber's background signal can be affected by the OCT signal from the sample, the determination of whether the optical probe is connected may not be accurate. In addition, this manner of evaluating the optical probe connection is inconvenient because a patient would have to be unnecessarily exposed to discomfort even before optical connection is confirmed.

On the other hand, when optical connection is confirmed prior to the catheter being used in the patient, not only patient's discomfort is avoided but also the optical probe connection is more accurately measured as the OCT signal of the sample will not interfere with the fiber's background signal. FIG. 5C illustrates a graph of the excitation laser light signal (dashed line), and exemplary Raman and/or auto fluorescence spectra (solid line) generated from optical probe fiber itself in response to being irradiated with the excitation laser light. In this manner, as illustrated in FIG. 5C, a return optical signal from the fiber 107 which has a wavelength range different from the wavelength of the excitation light, can be detected independently from the excitation light using a simplified optical system. Specifically, as shown in FIG. 5C, the Raman and/or auto-fluorescence light generated by the fiber itself can be accurately separated from excitation light with the optical filter 320 in the beam combiner 300 of the PIU 150. The optical filter 320 can be implemented as a notch filter specifically designed to block only a narrow band of wavelengths centered on the wavelength of the excitation light. In this manner, since the wavelength of the return optical signal is higher than the wavelength of the excitation signal, the intensity of the return signal will be unobstructed by the optical filter 320. Alternatively, the optical filter 320 can be implemented as a band-pass filter specifically designed to block wide band of wavelengths lower than the wavelengths of the Raman and/or fluorescence light returning from the fiber 107. In this manner, since the wavelength of the return optical signal is higher than the wavelength of the bandpass filter, the intensity of the return signal will still be unobstructed by the optical filter 320. The separated Raman and/or auto-fluorescence signals unobstructed by the optical filter 320 and undisturbed by any sample signals can accurately detected by the fluorescence detector 122, and then processed by computer 190 to determine the optical probe connection status as described in more detail herein below (with reference to FIG. 9).

When the optical probe is disconnected, or not properly aligned with the optics inside the PIU 150, the signal detected by the fluorescence detector 122 is very small (almost zero); that detected signal corresponds to noises such as thermal and/or electrical noise. On the other hand, when the optical probe is properly connected, the signal detected by the fluorescence detector 122 becomes high.

FIG. 5E illustrates an exemplary detection signal that can be used to determine whether or not the optical probe 450 of catheter 160 is appropriately connected to the catheter console. As illustrated in FIG. 5E, when a detected Raman and/or auto-fluorescence signal is below a predetermined intensity threshold, the optical probe is considered to be in an optically disconnected (OFF) state. Conversely, when a detected Raman and/or auto-fluorescence signal is equal to or above the predetermined intensity threshold, the optical probe is considered to be in appropriate optical communication (ON) with the catheter console.

The detector required to produce the signal illustrated in FIG. 5E preferably senses the return signal of the fiber 107 in a wavelength range of about 640 to 900 nm. The wavelength range of the detector is designed with either an optical low-pass filter, a high-pass filter, a band-pass filter, or any combination thereof used in the beam combiner 300 in the PIU 150, as shown in FIG. 3A. When a spectrometer is used instead of the fluorescence detector or in combination with the fluorescence detector, the system is able to obtain not only the intensity, but also the specific spectrum of the return optical signal, so that the system is able to easily differentiate the origin of the spectrum based on the signature spectrum of, for example, materials of the core and/or cladding of the fiber 107. The signature spectrum can be used to determine whether the return optical signal is being generated from the optical probe itself or from substances (e.g., biological contaminants or dirt) not appropriate for medical imaging. On the other hand, when a single detector such as photodiode, avalanche photodiode, or photomultiplier is used as the fluorescence detector 122, the detection sensitivity becomes high, which is advantageous for detecting even weak signals Raman scattering and/or fluorescence return signal. In this case too, the use of a more sensitive detector can ensure that even minor failures (misalignment, bending, etc.) of the fiber catheter are more easily detected.

As shown in FIG. 5D, silica fiber materials pumped with excitation light of 633 nm can generate a Raman scattering spectrum having multiple peaks at 655, 663, 675 nm (indicated by solid dark arrow pointing down). Therefore, the peak wavelength of one or more of signals at 655, 663, and 675 nm can be used to detect the status of optical probe connection. In this case, an optical detector with narrow band sensitivity may suffice to detect the optical probe connection. Naturally, it is also good to detect the intensity of the return signal in the wavelength range from 640 to 700 nm where the Raman signals are high, and then determine the optical probe connection based on a statistical analysis (e.g., averaging or integrating) of the signal as a whole. In this case, an optical detector with corresponding broad wavelength sensitivity would be necessary.

However, since the catheter system can be applicable to many different uses, the excitation light is not limited to 633 nm. Although the Raman spectrum of silica fiber materials appears with substantially the same energy shifts ($530\ cm^{-1}$, $715\ cm^{-1}$, $983\ cm^{-1}$) from the excitation laser wavelength, the excitation wavelength can be changed from 633 nm to other specific wavelengths such as 404, 450, 520, 635, 650, 670, 740, 785, 830 nm. Therefore, in the case of changing the excitation wavelength, the detector wavelength range also needs to be changed with the same energy shift amount as that of the Raman shift. In this regard, it should be noted that excitation wavelengths greater than 830 nm may need to use near infrared sensitive detectors.

On the other hand, the auto-fluorescence from the fiber appears high at around 660 to 720 nm. Therefore, the fluorescence detector 122 also needs to be adjusted to detect the auto-fluorescence at this wavelength range of 660 to 720 nm. Theoretically, the auto-fluorescence wavelengths do not change even when the excitation wavelength is changed. When the optical fiber 107 is a double clad fiber (DCF), the Raman scattering and/or auto-fluorescence signal are efficiently delivered through the clad (cladding) of the DCF so that the detection/collection efficiency becomes high. The Raman scattering and/or auto-fluorescence signal are generated within the optical fiber itself so that this method is not sensitive to catheter sheath materials, distal optics fabrication tolerance, or the length of the optical fiber (most catheters typically use the same fiber length). Therefore, highly reliable detection of the optical probe connection can be achieved with this method.

<Tissue Auto-Fluorescence>

The specific catheter system 100 illustrated in FIG. 1 is used for, among other things, spectroscopic analysis of bodily lumens, such as blood vessels. To that end, fluorescence sub-system delivers light or other radiation from excitation light source 810 to the distal end of catheter 160, where the light exits a catheter window and illuminates an area near the distal end. With this catheter probe connection, tissue auto-fluorescence can be acquired during measurements. Advantageously, however, the fluorescence signal obtained from the fiber itself during optical probe connection detection can be used to more accurately determine the auto-fluorescence spectrum of the tissue being examined.

Figure 6A:
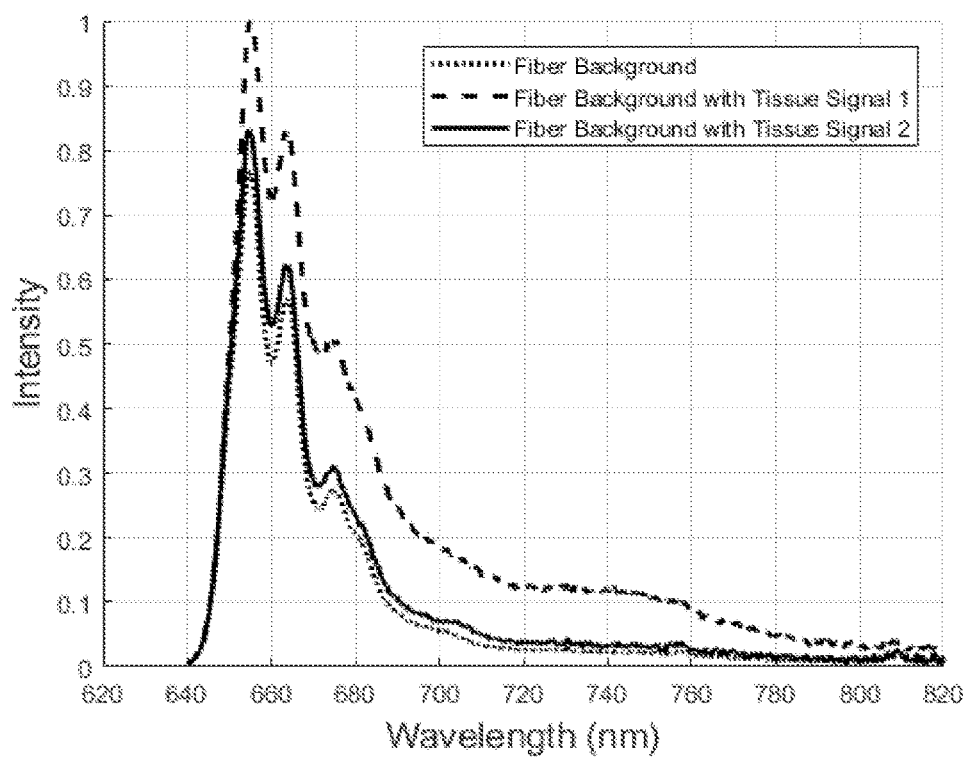
FIG. 6A shows a graph of spectra of fiber background and tissue signals obtained when irradiating a sample with excitation light using the optical probe of the catheter.
Figure 6B:
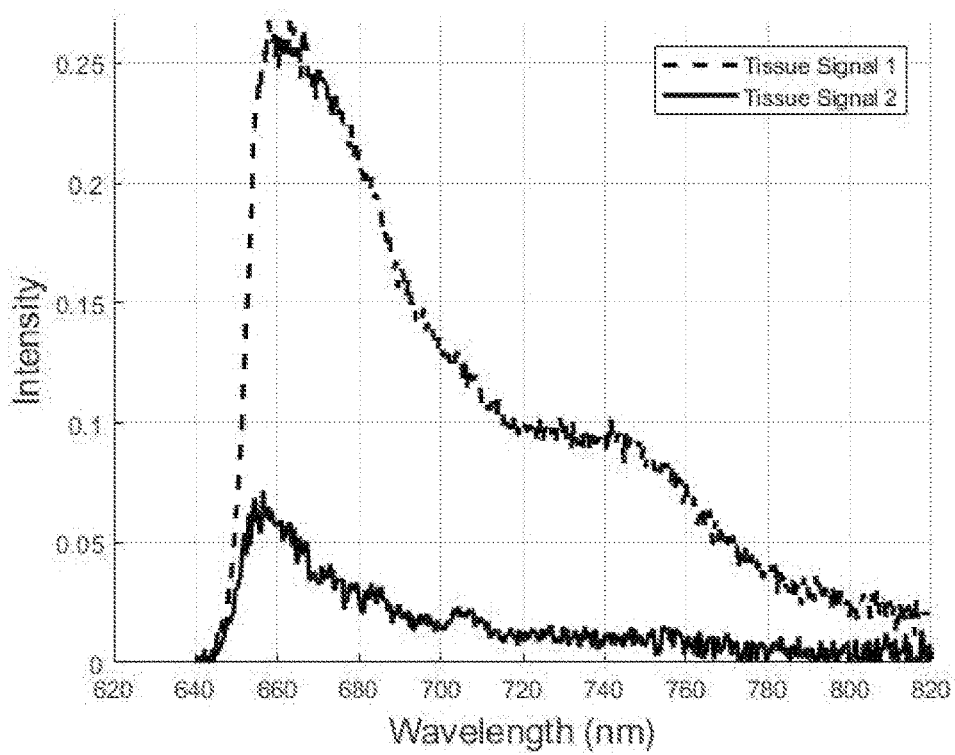
FIG. 6B is a graph showing spectra of tissue signals after removing the fiber background signal.

FIG. 6A is a graph showing an exemplary fiber background spectrum and fluorescence spectra of tissue auto-fluorescence signals. The auto-fluorescence spectrum and intensity from tissues depends on tissue characterizations, for example, the lipid rich plaque (tissue signal 1) has high intensity compared with normal vessel tissue (tissue signal 2), in FIG. 6A. The fiber background of the spectrum shown in FIG. 6A is high, but it is relatively constant so that the actual fluorescence tissue signals are calculated by subtracting the fiber background signal that is acquired before and/or after the actual tissue measurement. The result of such subtraction is shown in FIG. 6B. The wavelength range of auto-fluorescence from the tissue is from approximately 640 nm to 820 nm. In this embodiment, fluorescence detector 122 (shown in FIG. 1) is a single sensor such as photodiode, an avalanche photodiode, a photomultiplier, or the like, which is configured to detect the fiber background signal, tissues signal 1, and the tissue signal 2 (shown in FIG. 6A). The intensity of auto-fluorescence signal is analyzed and displayed, by computer 190, for example, as shown in FIG. 6B. The wavelength range of fluorescence detector 122 can be adjusted, for example, by using filters, to match with the wavelength range from approximately 650 to 810 nm to maximize SNR where it becomes the highest.

Figure 7A:
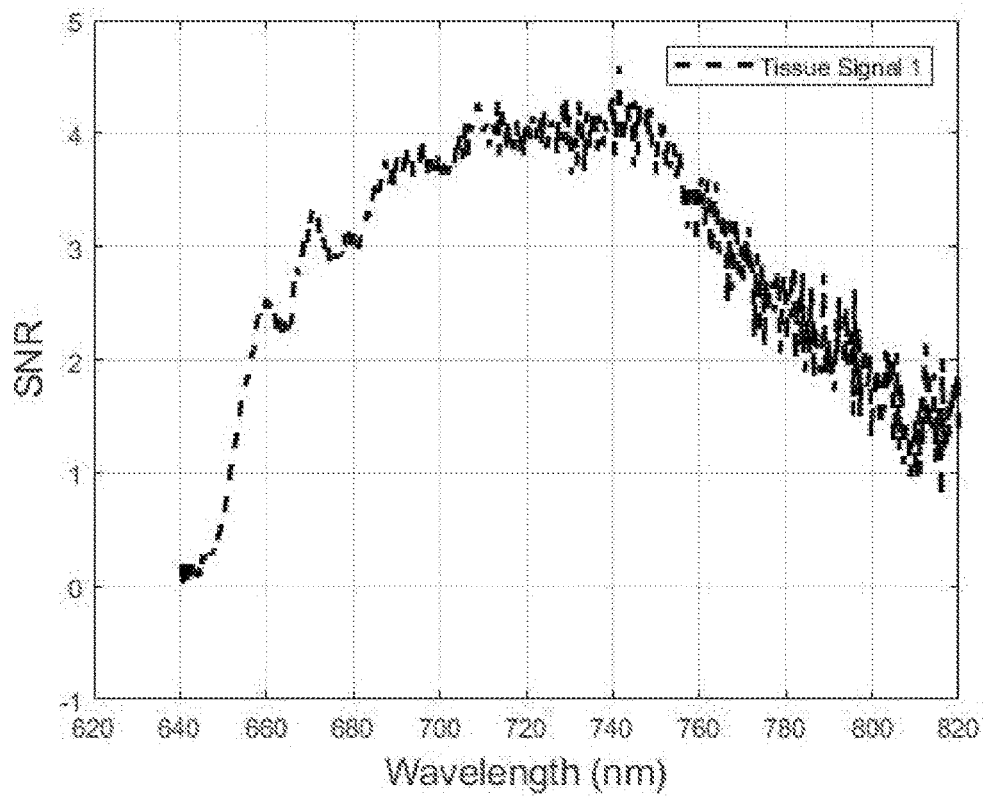
FIG. 7A shows a graph of Signal-to-Noise Ratio (SNR) calculation results from measured fiber background and a tissue signal.
Figure 7B:
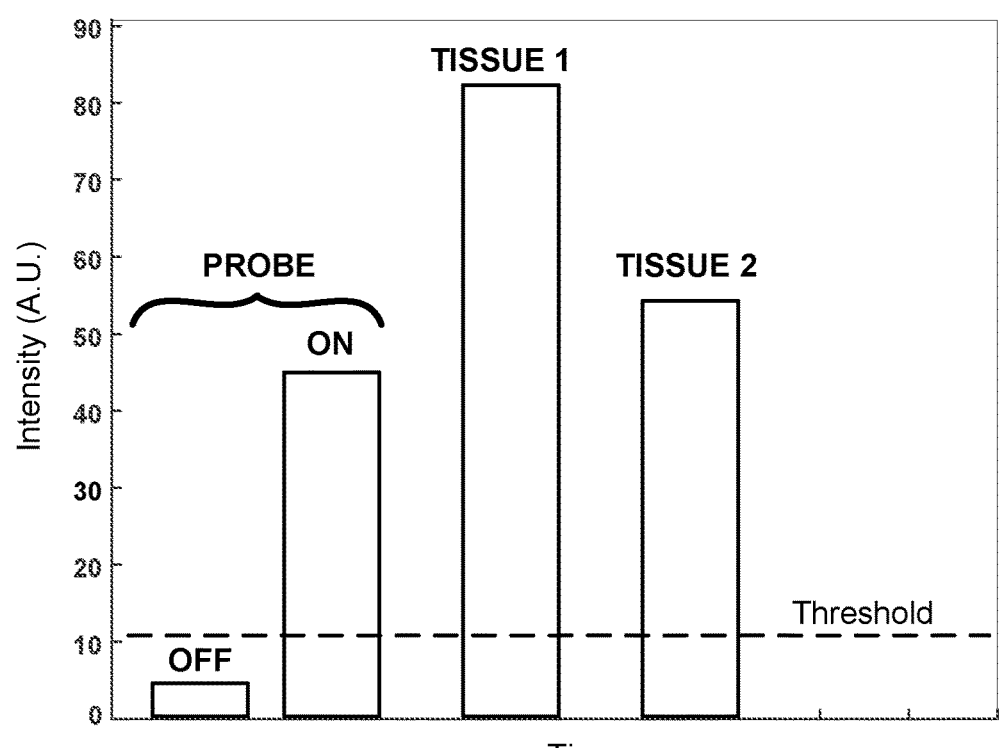
FIG. 7B shows a graph of auto-fluorescence intensity levels detected from Raman and/or auto fluorescence signals obtained from the fiber of the optical probe.

FIG. 7A shows a Signal to Noise Ratio (SNR) from tissue signal 1 after correcting for fiber background noise. Note, the noise is assumed from shot noise from fiber background noise. FIG. 7B is a graph showing intensity levels of optical probe connection detection and tissue fluorescence measurements as function of time. In FIG. 7B, the intensity levels of optical probe connection show the exemplary functionality of catheter system 100, where at an initial time the probe is in an OFF state when the Raman and/or auto-fluorescence signal is below a given threshold. As time elapses, the probe signal becomes equal to or higher than the given threshold, and therefore the probe is in an ON state. Thereafter, when catheter system 100 has ensured that the optical probe of the catheter is appropriately connected, the tissue signal 1 (TISSUE 1) and tissue signal 2 (TISSUE 2) can be safely and accurately measured.

<OCT and Auto-Fluorescence Measurements>

Imaging of coronary arteries by intravascular OCT and auto-fluorescence can be achieved with the catheter system 100 described in the embodiment of FIG. 1. The system can be used, for example, to see vessels (e.g., coronary artery) to diagnose stenosis regions and high-risk plaque presence. In addition, the system 100 has a particular feature to detect and/or monitor connection of catheter probes by using Raman and/or auto-fluorescence signals acquired from the optical fiber itself before the catheter is applied to the patient. With this feature, the catheter system 100 is able to take measures to prevent from secondary harms, and notify users of potential errors when the catheter probe is not yet connected or becomes un-expectedly disconnected. The process of detecting and evaluating the status of the optical probe connection to the catheter console is described in S902-S910 of FIG. 9. However, ensuring appropriate optical probe connection to the catheter console is only part of the function of the multi-modality system 100 described herein. As previously mentioned, the system 100 is applicable for imaging of coronary arteries and other similar imaging applications where catheters and/or endoscopes are necessary.

<System Control and Image Processing>

Figure 8A:
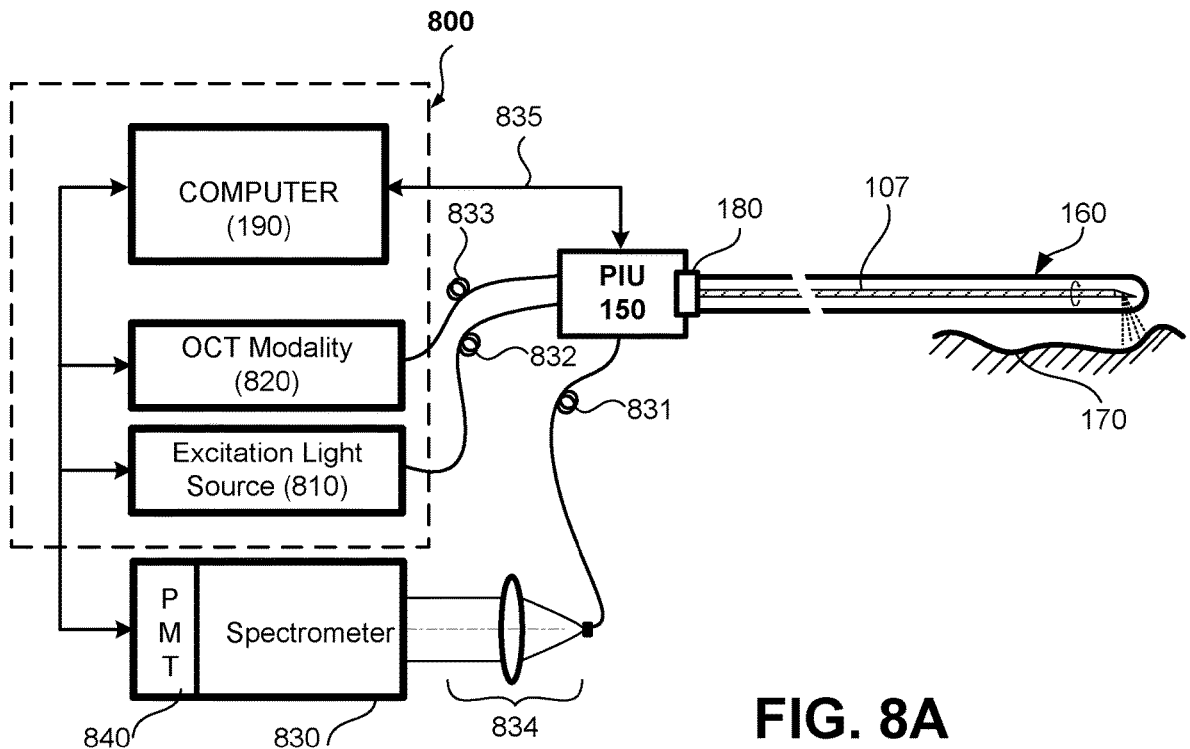
FIG. 8A illustrates an exemplary implementation of an electronic console connected to the multimodality catheter.
Figure 8B:
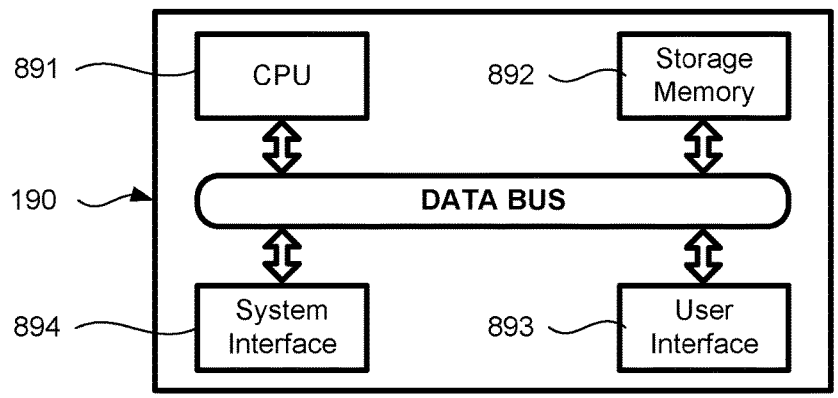
FIG. 8B is a block diagram of an exemplary computer control system for performing control and image processing in the multimodality catheter system.

FIG. 8A illustrates an exemplary implementation of an electronic system console 800 connected to the multimodality catheter 160. FIG. 8B is a functional block diagram of an exemplary computer control system for performing control and image processing in the multimodality catheter system. A system console 800 to acquire multi-modality images using the catheter 160 is shown in the diagram of FIG. 8A. The system console 800 includes or is connected to, for example, an OCT modality 820, the excitation light source 810, a detector 840, spectrometer 830, a patient interface unit (PIU) 150, and computer 190. The system console 800 is connected to the PIU 150 via one or more cables (a cable bundle 835). The optical catheter 160 has a proximal end attachable to the PIU 150 and a distal end thereof configured to house therein the optical probe which is used to illuminate an area of a sample located at a working distance from the distal end.

Similar to FIG. 1, the OCT modality 820 in FIG. 8A can include an interferometer and a tunable laser source or a lamp that outputs light of broadband spectrum in the infrared range of about 1250 to 1350 nm. The excitation light source 810 can be a laser or an LED that outputs light of a single color (single wavelength) or a narrow band spectrum. The range of the wavelength of the excitation light source 810 can be within the visible region, which is from about 400 nm thorough 800 nm. However, other wavelengths in the near-infrared range may also be used. In the exemplary system console Boo, OCT light can be directly guided or otherwise coupled into an OCT source fiber 833; the excitation light from excitation light source 810 can be similarly directly guided or otherwise proved into an excitation source fiber 832. The light from the OCT light source and from the excitation light source are transferred to the optical catheter 160 by the optics of the beam combiner 300 arranged within the PIU 150.

The catheter 160 is connected at its proximal end thereof to the PIU 150 via the catheter connector 180. The catheter 160 includes the fiber 107 and an assembly of distal optics (optical probe described above) arranged within the distal end of the catheter. In this manner, illumination light emitted from OCT light source of the OCT modality 820 and excitation light from light source 810 can be delivered to the distal optics of catheter 160, and then directed by a diffracting element (grating) or reflecting element (mirror) onto an area of sample 170. The light scattered back from an area of the target sample (e.g., tissue) can be collected by the cladding of fiber 107, or by detecting fibers arranged around the distal end of optical probe (see FIGS. 10A-10B). The collected light is guided back to the PIU 150 by the cladding of fiber 107, or the one or more detection fibers other than the fiber 107. In the PIU 150, the beam combiner 300 selectively guides the measurement results (fluorescence and OCT scattered light) to one or more of detectors 121 and 122.

For detection of optical probe connection, as described elsewhere in this specification, the catheter 160 is preferably not yet poisoned within a patient. Therefore, during detection of the optical probe connection, light from a target sample is not collected. Instead, the excitation light is activated for a short period of time to illuminate the fiber inside the catheter 160, whereby the materials of the core and/or cladding of the fiber undergo a process of Raman scattering and/or fluorescence emission. The Raman scattering and/or fluorescence light generated from the fiber 107 returns to the console and is detected by the detector/spectrometer 830. Since fiber output from the fiber 831 is dispersive, the fiber connector is placed closely near the detector, or a collimating/dispersing optical system 834 is used. Specifically, the Raman scattering and/or fluorescence light returned from the fiber 107 is guided by a fiber 831 from the PIU 150 to spectrometer/detector 830. In this manner, the intensity of the Raman and/or fluorescence signal returned from the fiber and optical probe, or the intensity of a selected wavelength can be accurately detected without being distorted by fluorescence or scattering from the sample. The function of detecting a selected wavelength of return optical signal can be performed by selecting a specific single wavelength or a specific wavelength range with the spectrometer or optical filters.

During actual medical imaging, by mechanically rotating the optical probe of catheter 160 with the FORJ, it is possible to obtain two-dimensional images of the target sample. On the other hand, during detection of optical probe connection, rotation of the optical probe can be avoided as long as a return optical signal including Raman and/of fluorescence spectra can be obtained. Computer 190 includes one or more microprocessors configured to control and operate the various parts of system console 800 by executing computer-executable instructions (program code). Computer 190 can also be programmed to evaluate the status of optical probe connection based on the return optical signal and to reconstruct images of a sample based on signals obtained from irradiating the sample.

FIG. 8B is a schematic functional diagram of exemplary computer hardware used to control for the multi-modality catheter system console 800 (and 100 in FIG. 1). As shown in FIG. 8B, the computer 190 includes a central processing unit (CPU) 891, a storage memory (ROM/RAM) 892, a user input/output (I/O) interface 893, and a system interface 894. The various components of the computer 190 communicate with each other via physical and logical data lines (DATA BUS).

Storage memory 892 includes one or more computer-readable and/or writable media, and may include, for example, a magnetic disc (e.g., a hard disk drive HHD), an optical disc (e.g., a DVD®, a Blu-ray®, or the line), a magneto-optical disk, semiconductor memory (e.g., a non-volatile memory card, Flash® memory, a solid state drive, SRAM, DRAM), an EPROM, an EEPROM, etc. Storage memory 892 may store computer-readable data and/or computer-executable instructions including Operating System (OS) programs, and control and processing programs.

The user interface 893 provides a communication interface (electronic connections) to input/output (I/O) devices, which may include a keyboard, a display (LCD or CRT), a mouse, a printing device, a touch screen, a light pen, an external optical storage device, a scanner, a microphone, a camera, a drive, communication cable and a network (either wired or wireless).

The system interface 894 also provides an electronic interface (electronic connection circuits) for one or more of the OCT light source 110, excitation light source 810, detector/spectrometer 830 (in FIG. 8A) or the detector 121 and detector 122 (in FIG. 1), data acquisition electronics DAQ1 (131) and DAQ (132), and the patient unit interface (PIU) 150. The system interface 894 may include programmable logic for use with a programmable logic device (PDL), such as a Field Programmable Gate Array (FPGA) or other PLD, discrete components, integrated circuitry (e.g., an Application Specific Integrated Circuit (ASIC)), or any other components including any combination thereof.

The function of the user interface 893 and of the system interface 894 may be realized at least in part by computer executable instructions (e.g., one or more programs) recorded in storage memory 892 and executed by CPU 891. Moreover, the computer 190 may comprise one or more additional devices, for example, components such as a communications or network interface for communicating with other medical devices, such as a Picture archiving and communication system (PACS).

<Catheter Connect and Disconnect Process>

Figure 9:
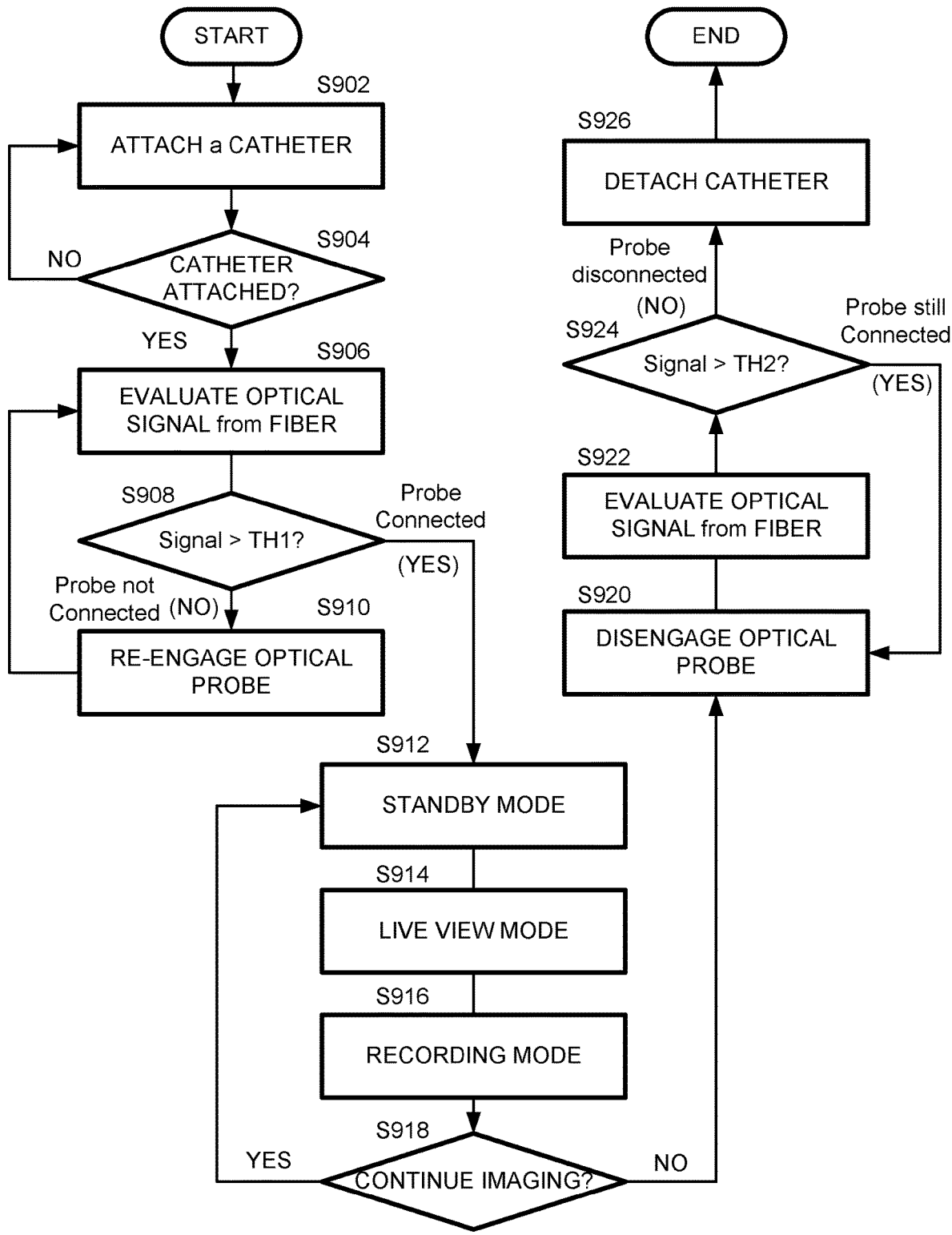
FIG. 9 illustrates an exemplary flow process for controlling the multimodality system to perform optical probe connection detection and image generation.

FIG. 9 shows an exemplary process (method) for catheter connection, sample measurement, and catheter disconnection. The process is performed based on the structure of the system described above with reference to FIG. 1. According to this process, the catheter system 100 becomes more reliable by adding detection and/or monitoring of optical probe connection at several steps of the process. Also, this process prevents from performing erroneous operations and from damage to the PIU and catheters.

In operation, as shown in FIG. 9, catheter connection is required at the beginning (START) of the process. The catheter handle is mechanically connected to the PIU by users. So catheter and the console are attached to each other at step 902. Specifically, at step S902 catheter handle connection occurs when a user manually connects the proximal end of catheter 160 to the PIU 150 (console). Once the catheter is connected, the connection is detected with a sensor such as touch sensors, optical sensors, and/or pressure sensors (not shown). The mechanical connection detected by a sensor is converted to an electrical signal, and then the electrical signal is transferred to the console of the system to recognize the catheter handle connection by executing software instructions with the CPU of computer 190.

Specifically, at step S904, the CPU of computer 190 runs a macro which confirms whether or not the catheter has been mechanically connected to the console. In the case that the CPU of computer 190 confirms that a catheter has been mechanically connected to the console, the process advances to step S906. In the event that the CPU of computer 190 cannot confirm that a catheter is connected to the console, the process enters a loop of steps S902 to S904 until a user actively connects a catheter to the PIU 150. In this loop, the console of catheter system 100 may issue a warning or prompt informing the user that a catheter has not been detected.

Evaluation of optical probe connection. At step S906, after a catheter has been determined to be connected to the console, but prior to using the catheter in a patient, the CPU of computer 190 controls the system to detect and evaluate an optical signal (a return optical signal) from the catheter. To that end, for example, the CPU of computer 190 controls the excitation light source 810 to emit a beam of excitation light, and then controls the fluorescence detector 122 to detected a signal returning from the fiber 107 of catheter 160.

For evaluation of the probe connection, when the signal of the fluorescence detector 122 crosses a certain threshold, the computer 190 judges the probe connections. At step S908, after activating the light source 810 and controlling the fluorescence detector 122 to detect a return signal, the CPU of computer 190 determines whether the signal output by detector 122 is greater than a predetermined threshold (TH1). If the return signal detected is greater than the threshold, the CPU determines that the optical probe is properly connected to the console, and the process proceeds to actual imaging measurement process (standby, live view, and recording mode). In the event that the return signal detected by fluorescence detector 122 is not greater than the threshold, the CPU determines that the optical probe is not properly connected to the console, and the process proceeds to S910.

Generally, when the catheter is mechanically connected to the console, the optical probe is automatically engaged to the PIU. However, when automatic engagement does not occur, at step S910, the CPU of computer 190 prompts the user to actively re-engage the optical probe to the console. For example, the CPU of computer 190 issues a visual or aural indication that the optical probe is not yet connected (or it is not properly connected), and requests the user to, for example, manually remove and reconnect the catheter 160 to the PIU 150. This event can occur, for example, in the case where the fiber or optical probe of the catheter 160 is broken or bent, or otherwise not able to transmit enough light therethrough. The system may ask users to operate the catheter to re-engage the optical probe and/or stop the probe engagement process to replace the damaged probe with new catheter. For evaluation of the probe connection, when the signal of the fluorescence detector 122 crosses threshold (TH1), the CPU of computer 190 judges the probe connection is appropriate. The loop of steps S906, S908 and S910 is repeatedly performed until the CPU of computer 190 makes a determination that a return optical signal detected by fluorescence detector 122 is above the predetermined threshold value (YES in step S908).

After the system confirms that the optical probe is successfully engaged and optically aligned, the system is ready for imaging, or it moves to a standby mode to wait for a measurement command. In an actual imaging operation, there are a standby mode (S912), a live view mode (S914), and a recording mode (S916), which are typical modes of a catheter system. In the standby mode, the catheter system stops any lasers and motors so the system does not generate any images, but simply waits for a user's command. In the live view mode, the system is actively imaging to show real-time (live view) images, e.g., during navigation of the catheter towards a region of interest, but does not record the live view images. In the recording mode, the system is fully operational to actively acquire and record images of a desired target location.

At step S918, the system is programed to prompt the user whether an imaging operation should continue or not. In the event that imaging should not continue (NO in S918), the system advances to step S920 and begins optical probe disengagement. Specifically, in step S920, the optical probe is automatically disengaged from the PIU 150 once a user sends a command to the console to eject the catheter. The optical fiber connector of the optical probe will be disconnected in this mode. Subsequently, at step S922, the system evaluates the optical signal detected by fluorescence detector 122; and at step S924 computer 190 of the system performs an evaluation of optical probe connection based on the signal detected by fluorescence detector 122.

Specifically at step S924, the system confirms that the optical probe is successfully disengaged (Probe disconnected), if the signal at the fluorescence detector 122 is less than a predetermined disconnection threshold (TH2). Otherwise if the signal detected at fluorescence detector 122 is still greater than the disconnection threshold (TH2), the system goes back to the optical probe disengagement step S920. In this step S920, the system may prompt users to operate probe disengagement. For evaluation of the probe connection, when the signal detected by the fluorescence detector 122 is below (crosses) the disconnection threshold (TH2), the computer 190 judges that the optical probe is disconnected. In this case, the process advances to step S926, where the system may issue a prompt to the user to mechanically disconnect the catheter from the system. Therefore, the loop of S920, S922 and S924 can be repeated until the system determines that the optical probe has been disconnected from the console and the signals of the fluorescence detector 122 are lower than the threshold (TH2).

After determining that the optical probe is disconnected, at step S926, the system may prompt users to remove catheter handle from the connector 180. Catheter handle disconnect occurs when the catheter handle is mechanically disconnected from the PIU 150 by users. Once the catheter is manually detached from the console the process can end or a new catheter can be mechanically attached.

In the flow process of FIG. 9, the threshold TH1 and the threshold TH2 can be established, for example, as a percentage of the expected intensity of the Raman scattering and/or fluorescence signal generated from the fiber itself. The expected intensity of the Raman scattering and/or fluorescence signal of the fiber may be obtained from the fiber's manufacturer, or may be obtained by experimental measurement. In a fiber-optic-based catheter, as described above, one or more light conducting fibers can be used to transmit light in both directions (illumination and collection). Propagation of light along optical fibers occurs because of the effect known as total internal reflection. Nevertheless, various loss-producing mechanisms such as launch coupling loss, fiber attenuation, splice losses, and connector losses reduce the intensity of the light transmitted from one end to the other of the catheter. In this regard, the general principles of the optical power budget for a fiber-optic communication link may be used to determine the expected intensity to be received by the fluoresce detector 122.

For example, in one embodiment, the threshold TH1 or the threshold TH2 can be determined based on the optical power P (e.g., 0 dBm=1 mW) of the excitation light source, the expected thermal noise $N_{th}$ of the detector, and any possible optical losses η due to fiber dispersion, connector losses, cross-talk, etc. In that case, the threshold TH1 for determining of whether the optical probe has been properly connected to the console at S908 can be, for example, 75% or higher than the intensity of the florescence signal expected to be received at the fluorescence detector 122. In this manner, a low signal (e.g., 30% of expected intensity) due to misalignment of the fiber connector or due to contamination (dirt or dust) in the fiber connection would prompt the user to review the connection or to change the catheter. On the other hand, the threshold TH2 for determining whether the optical probe has been fully disconnected from the console at step S924 can be, for example, 10% or lower than the intensity of the fluorescence signal expected to be received at the fluorescence detector 122. In this manner, the user can ensure that the optical probe is completed disengaged and that any signal present at the fluorescence detector 122 is only due to thermal or spurious noise. In other embodiments, the threshold TH1 and the threshold TH2 can be set to a similar value, for example, as a percentage (e.g., 50%) of the expected intensity of the fluoresce signal. In this case, when the signal at S908 is equal to or greater than TH1, the system can determine that the optical probe of the catheter is properly connected to the console. And conversely, when the signal at S924 is below TH2 (where TH2≈TH1), the system can determine that the optical probe of the catheter is disconnected from the console.

Figure 10A:
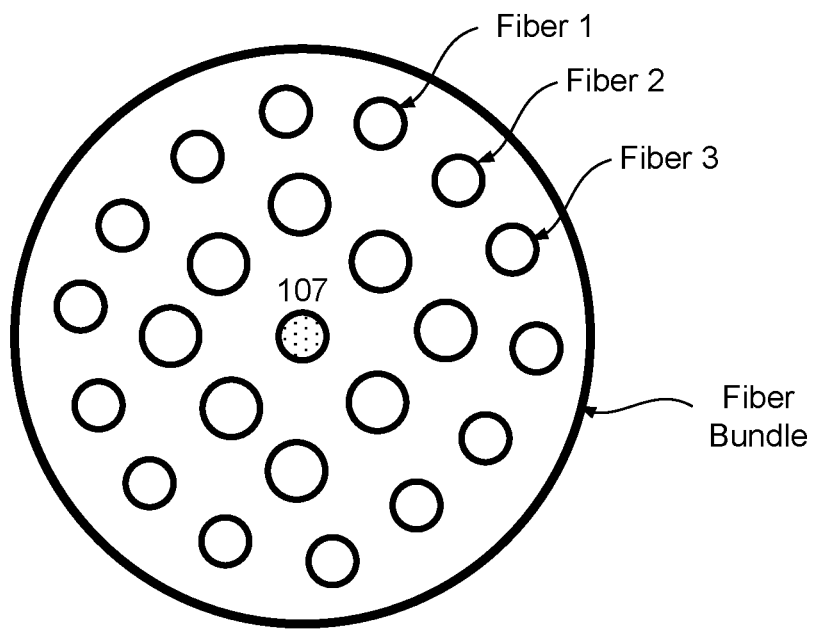
FIG. 10A shows a cross-sectional view of an exemplary fiber bundle, and FIG. 10B show the cross-section of an exemplary multi-fiber structure, which are examples of fiber optics arrangements for the multi-modality catheter system.
Figure 10B:
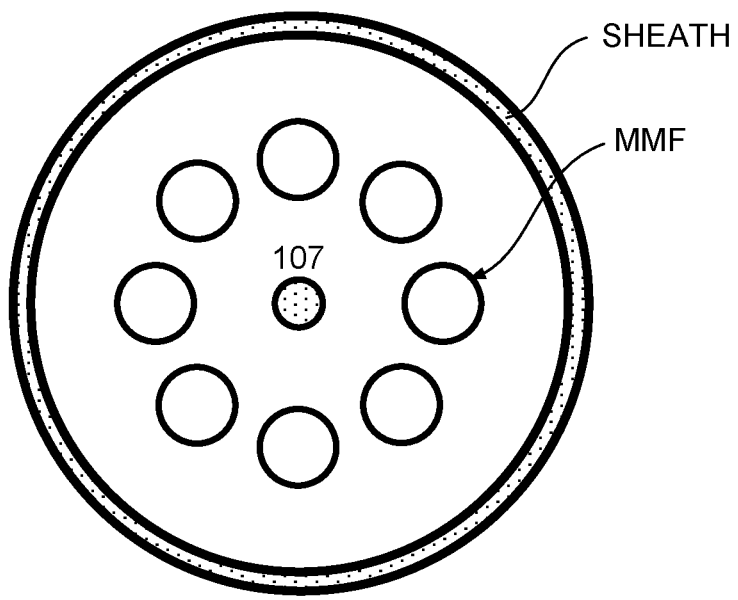

As described above, the catheter may include a single double-clad fiber (DCF) for delivering and collecting light to and from the sample. However, the catheter can be modified to include a fiber having more than two claddings (a multi-cladding fiber), or a fiber bundle, or a holey fiber (a photonic crystal microstructure fiber), or a custom-made multi-fiber structure, or combinations thereof. Furthermore, the catheter may be replaced by an endoscope having the optical probe formed of a bundle of one or more optical fibers. FIG. 10A shows a cross-sectional view of an exemplary fiber bundle, and FIG. 10B shows a multi-fiber structure. In both FIGS. 10A and 10B, a center fiber is fiber 107 used for delivering and collecting the OCT signal, while the plurality of fibers (Fiber 1, Fiber 2, Fiber 3 . . . , Fiber n) surrounding the center fiber are either multimode fibers (MMF) or single mode fibers used for collecting the backscattered and fluorescence light from the sample.

While the present patent application has been described with reference to exemplary embodiments, it is to be understood that the invention is not limited to the disclosed exemplary embodiments. The scope of the following claims is to be accorded the broadest interpretation so as to encompass all possible modifications and equivalent structures and functions. To that end, it must be noted that the terminology used herein is for the purpose of describing particular embodiments only and is not intended to be limiting.

It should be further noted that operations performed as method steps/processes or otherwise described herein in algorithm form are those operations requiring physical manipulations of physical quantities, which usually but not necessarily, take the form of electrical or magnetic signals capable of being stored, transferred, combined, transformed, compared, and otherwise manipulated electronically. Therefore, unless specifically stated otherwise, it will be apparent to those skilled in the art that throughout the above description, discussions utilizing terms such as "processing" or "computing" or "displaying" or "calculating" or "comparing, "calibrating" "generating" or "determining" and the like, refer to the action and processes of a computer system, or similar electronic component, that manipulates and transforms data represented as physical (electronic) quantities within the computer system's registers and memories into other data similarly represented as physical quantities within the computer system memories or registers or other such information storage, transmission, or display device.

Other Definitions

Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", may be abbreviated as "/", and it includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

LIST OF EXEMPLARY REFERENCES

The following non-patent literature (NPL) and patent publications, which are considered "nonessential material", are hereby incorporated by reference herein in their entirety:

1. Motz et al., "Optical Fiber Probe for Biomedical Raman Spectroscopy", Applied Optics Vol. 43, No. 3, 20 Jan. 2004;
2. Ma et al., in "Fiber Raman background study and its application in setting up optical fiber Raman probes", Appl. Opt. 1996;
3. Walrafen et al., in "Raman Spectral Characterization of Pure and Doped Fused Silica Optical Fibers", Applied Spectroscopy, Volume 29, Number 4, 1975, pages 337-344.
4. Patent publications include: U.S. Pat. Nos. 8,758,223, 6,009,220, 5,625,450, 7,132,645, and 6,069,691; and pre-grant publications (PGPUB) US 2008/0304074 (Brennan), US 2012/0176613 (Marple et al.), and US 2003/0077043 (Hamm et al.).

What is claimed is:

1. A catheter system, comprising:
an electronic console;
an excitation light source configured to emit excitation radiation;
a catheter having a proximal end attachable to the console and a distal end configured to house therein an optical probe;
an optical fiber configured to transmit from the console to the optical probe excitation radiation emitted from the excitation light source, and configured to collect an optical response signal having a wavelength longer than that of excitation radiation;
a detector configured to detect intensity or wavelength of the optical response signal; and
a processor configured to determine, based on the detected intensity or wavelength, whether the optical probe is properly connected to the console,
wherein the optical response signal is generated by at least one of photon scattering and auto-fluorescence within the optical fiber itself in response to transmitting the excitation radiation therethrough.

2. The catheter system according to claim 1,
wherein the optical fiber is a double clad fiber comprising a core concentric with the longitudinal axis of the optical fiber, an inner cladding surrounding the core, and an outer cladding surrounding the inner cladding.

3. The catheter system according to claim 2,
wherein the optical response signal is an auto-fluorescence signal generated from dopant materials used to form the inner and/or the outer cladding of the optical fiber, the auto-fluorescence signal being generated in response to transmitting the excitation radiation through the inner and/or the outer cladding of the optical fiber.

4. The catheter system according to claim 1,
wherein the optical response signal is a Raman scattering signal generated from the optical fiber itself in response to transmitting the excitation radiation therethrough.

5. The catheter system according to claim 4,
wherein the optical fiber is a double clad fiber comprising a core concentric with the longitudinal axis of the optical fiber, an inner cladding surrounding the core, and an outer cladding surrounding the inner cladding, and
wherein the Raman scattering signal is generated from silica material used to form the core of the optical fiber, the Raman scattering being generated in response to transmitting the excitation radiation through the core of the optical fiber.

6. The catheter system according to claim 1, wherein optical fiber is a double clad fiber having a central longitudinal axis extending from the proximal end to the distal end of the catheter, the double clad fiber comprising a core concentric with the longitudinal axis, an inner cladding surrounding the core, and an outer cladding surrounding the inner cladding.

7. The catheter system according to claim 1, further comprising a laser source configured to emit the excitation radiation, wherein the wavelength of the excitation radiation is in the range of about 400 to 800 nm.

8. The catheter system according to claim 1, wherein processor determines whether the optical probe is properly connected to the console by analyzing the detected optical return signal at a specific wavelength range.

9. The catheter system according to claim 1, wherein processor determines whether the optical probe is properly connected to the console by analyzing the detected optical return signal at a specific wavelength.

10. The catheter system according to claim 1, further comprising a free-space beam combiner configured to separate the excitation light from the return optical signal, wherein the free-space beam combiner includes one or more optical filters configured to block the excitation light from being returned to the detector.

11. The catheter system according to claim 1, further comprising a radiation source different from the excitation source,
wherein the optical response signal is generated as a function of auto-fluorescence or Raman scattering of the optical fiber itself in response to transmitting the excitation radiation therethrough,
wherein the radiation source emits a radiation of first wavelength, and the radiation of first wavelength emitted from the radiation source is coupled into the optical probe via the optical fiber, and radiation of a second wavelength is collected by the optical probe from an area surrounding a distal end of the optical probe, and
wherein the processor controls the radiation source to emit the radiation of first wavelength based on a determination of whether the optical probe is properly connected to the console.

12. The catheter system according to claim 1, further comprising:
a patient interface unit (PIU) operatively connected to the proximal end of the catheter,
wherein the PIU includes a fiber optic rotary joint (FORJ), a rotational motor and translation stage,
wherein the optical fiber is a double clad fiber disposed in a protective sheath,
wherein the FORJ is configured to provide uninterrupted transmission of the excitation radiation having a first wavelength and OCT radiation having a second wavelength from one or more light sources other than the excitation light source, and
wherein the FORJ is configured to provide uninterrupted transmission of collected radiation to the detector while rotating the double clad fiber within the catheter during a pullback operation.

13. A method of determining optical connection of a catheter to an electronic console, the catheter having a proximal end attachable to the console, a distal end configured to house therein an optical probe, and an optical fiber that extends from the distal end to the optical probe, the method comprising:
connecting the proximal end of the catheter to the console;
transmitting excitation radiation from an optical source to the optical probe through the optical fiber, and collecting an optical response signal having a wavelength longer than that of excitation radiation;

detecting the intensity or wavelength of the optical response signal; and determining, based on the detected intensity or wavelength, whether the optical probe of the catheter is properly connected to the console, wherein the optical response signal is generated by at least one of photon scattering and auto-fluorescence within the optical fiber itself in response to transmitting the excitation radiation therethrough.

14. The method according to claim 13,
wherein the optical fiber is a double clad fiber comprising a core concentric with the longitudinal axis of the fiber, an inner cladding surrounding the core, and an outer cladding surrounding the inner cladding.

15. The method according to claim 14,
wherein the optical response signal is an auto-fluorescence signal generated from dopant materials used to form the inner and/or the outer cladding of the fiber, the auto-fluorescence signal being generated in response to transmitting the excitation radiation through the inner and/or the outer cladding of the optical fiber.

16. The method according to claim 13,
wherein the optical response signal is a Raman scattering signal generated from the optical fiber itself in response to transmitting the excitation radiation therethrough.

17. The method according to claim 16,
wherein the optical fiber is a double clad fiber comprising a core concentric with the longitudinal axis of the fiber, an inner cladding surrounding the core, and an outer cladding surrounding the inner cladding, and
wherein the Raman scattering signal is generated from silica material used to form the core of the optical fiber, the Raman scattering signal being generated in response to transmitting the excitation radiation through the core of the optical fiber.

18. The method according to claim 13, wherein the step of transmitting excitation radiation through the optical fiber includes emitting the excitation radiation in a wavelength range of about 400 nm to 800 nm.

19. The method according to claim 13, wherein the step of determining whether the optical probe is properly connected to the console includes analyzing the detected optical return signal at a specific wavelength range.

20. The method according to claim 13, wherein the step of determining whether the optical probe is properly connected to the console includes analyzing the detected optical return signal at a specific wavelength.

21. The method according to claim 13, further comprising:

separating the excitation light from the return optical signal using a free-space beam combiner, wherein the free-space beam combiner includes one or more optical filters configured to block the excitation light for being returned from the optical fiber to the console; and detecting the return optical signal without detecting excitation light.

22. The method according to claim 13, further comprising:

emitting OCT radiation different from the excitation radiation, in response to determining that the optical probe of the catheter is properly connected to the console.

23. The method according to claim 13, wherein the step of determining whether the optical probe of the catheter is properly connected to the console includes determining whether the detected intensity of the optical return signal is higher than a predetermined threshold value.

24. An apparatus for testing whether an optical probe is properly connected to a device, comprising:

a laser source configured to output an excitation beam;

an optical fiber configured to transmit the excitation beam from the laser source to the optical probe, and configured to collect an optical response signal generated from the optical fiber itself;

a detector configured to detect intensity or wavelength of the optical response signal; and a processor configured to determine, based on the detected intensity or wavelength, whether the optical probe is properly connected to the device, wherein the optical response signal is generated by at least one of photon scattering and auto-fluorescence within the optical fiber itself in response to transmitting the excitation beam therethrough, and wherein the optical response signal has a wavelength longer than that of the excitation beam.

25. The apparatus according to claim 24, further comprising:

an OCT light source configured to output an irradiation beam;

wherein the optical fiber transmits the irradiation beam from the OCT light source to the optical probe, and the optical probe directs the irradiation beam onto a sample, in response to the processor determining that the optical probe is properly connected to the device.

* * * * *